US008378064B2

(12) United States Patent
Grinstaff et al.

(10) Patent No.: US 8,378,064 B2

(45) Date of Patent: Feb. 19, 2013

(54) HYDROPHILIC POLYMERS AS MEDICAL LUBRICANTS AND GELS

(75) Inventors: Mark W. Grinstaff, Brookline, MA (US); Michel Wathier, Brighton, MA (US)

(73) Assignee: Trustees of Boston University, Boston, MA (US)

(*) Notice: Subject to any disclaimer, the term of this patent is extended or adjusted under 35 U.S.C. 154(b) by 423 days.

(21) Appl. No.: 12/301,410

(22) PCT Filed: May 18, 2007

(86) PCT No.: PCT/US2007/011888

§ 371 (c)(1),
(2), (4) Date: Apr. 3, 2009

(87) PCT Pub. No.: WO2007/136738

PCT Pub. Date: Nov. 29, 2007

(65) Prior Publication Data

US 2009/0208589 A1 Aug. 20, 2009

Related U.S. Application Data

(60) Provisional application No. 60/801,751, filed on May 19, 2006.

(51) Int. Cl.

| | |
|---|---|
| ***A61K 38/00*** | (2006.01) |
| ***A61K 47/00*** | (2006.01) |
| ***A61K 31/715*** | (2006.01) |
| ***C07K 2/00*** | (2006.01) |
| ***C07K 4/00*** | (2006.01) |
| ***C07K 5/00*** | (2006.01) |
| ***C07K 7/00*** | (2006.01) |
| ***C07K 14/00*** | (2006.01) |
| ***C07K 16/00*** | (2006.01) |
| ***C07K 17/00*** | (2006.01) |
| ***C07H 1/00*** | (2006.01) |
| ***A01N 25/00*** | (2006.01) |
| ***A01N 43/04*** | (2006.01) |

(52) U.S. Cl. .................... 530/300; 536/123.1; 514/773; 514/777; 514/54

(58) Field of Classification Search .................. 530/300; 536/123.1; 514/773, 777, 54

See application file for complete search history.

(56) References Cited

U.S. PATENT DOCUMENTS

| | | | | |
|---|---|---|---|---|
| 4,511,559 | A | 4/1985 | Szendrei et al. | |
| 5,676,964 | A * | 10/1997 | Della Valle et al. | 424/423 |
| 5,827,937 | A * | 10/1998 | Ågerup | 536/123.12 |
| 5,922,340 | A | 7/1999 | Berde et al. | |
| 6,046,187 | A | 4/2000 | Berde et al. | |
| 2002/0141967 | A1 | 10/2002 | Williams et al. | |
| 2003/0058812 | A1* | 3/2003 | Kendall et al. | 370/322 |

FOREIGN PATENT DOCUMENTS

| | | | |
|---|---|---|---|
| CA | 228695 | A | 2/1923 |
| DE | 19716312 | | 10/1998 |
| EP | 1710257 | A1 | 11/2006 |
| WO | WO02/10231 | A2 | 2/2002 |
| WO | WO03000191 | * | 1/2003 |
| WO | WO-03000191 | | 1/2003 |
| WO | WO-2005035588 | | 4/2005 |
| WO | WO2005097869 | * | 10/2005 |
| WO | WO-2005097869 | A1 | 10/2005 |
| WO | WO2011/109681 | A1 | 9/2011 |

OTHER PUBLICATIONS

Novak et al. J. Am. Chem. Soc. 1988, 110, 960-961.*
Barrow et al., "The structure of a novel polysaccharide isolated from *Zymomonas mobilis* determined by nuclear magnetic resonance spectroscopy", European Journal of Biochemistry, 1984, 145: 173-179.
Buchmeiser, M.R. et al., J. Am. Chem. Soc., 1997, 119: 9166-9174.
Dwek, R.A. et al., Ann. Rev. Biochem., 1993, 62: 65-100.
Fraser, C. and Grubbs, R.H. , Macromolecules, 1995, 28: 7248-7255.
Havard, J.M. et al., Macromolecules, 1999, 32: 86-94.
International Search Report for PCT/US07/11888 (Jan. 2008).
Kasuya, M.C. and Hatanaka, K., Macromolecules, 1999, 32: 2131-2136.
Kiely, D.E. et al., J. Am. Chem. Soc., 1994, 116: 571-578.
Kishore-Kumar, R. et al., Clin. Pharmacol. Ther., 1990, 47: 305-312.
Kjellen, L. et al., Ann. Rev. Biochem., 1991, 60: 443-475.
Lasky, L.A., Science, 1992, 258: 964-969.
Max, B.M. et al., Neurology, 1988, 38: 1427-1432.
Max, M.B. et al., Neurology, 1987, 37: 589-596.
Mortell, K.H. et al., J. Am. Chem. Soc., 1994, 116: 12053-12054.
Novak, B.M. and Grubbs, R.H. , J. Am. Chem. Soc., 1988, 110: 960-961.
Okada, M. et al., Makromol. Chem., 1978, 179: 949-958.
Schwab, P. et al., Angewandte Chemie International Ed. Eng., 1995, 34: 2039-2041.
Schwab, P. et al., J. Am. Chem. Soc., 1996, 118: 100-110.
Sharon, N. and Lis, H., Science, 1989, 246: 227-234.
Sharon, N., Sci. Amer., 1980, 254: 90-116.
Ventafridda, V. et al., Pain, 1990, 43: 155-162.
Weiss, W.I. et al., Nature, 1992, 360: 127-134.
Written Opinion for PCT/US07/11888 (Jan. 2008).
Yoshida, T. et al., J. Polymer Sci. A: Polymer Chem., 1998, 36: 841-850.

(Continued)

*Primary Examiner* — Fereydoun G Sajjadi
*Assistant Examiner* — Genevieve S Alley
(74) *Attorney, Agent, or Firm* — Choate, Hall & Stewart, LLP; Brenda Herschbach Jarrell; Charles E. Lyon

(57) ABSTRACT

The present invention provides new biopolymers which mimic the properties of natural polysaccharides found in vivo. The inventive polysaccharides can be used as visco-supplements, viscoelastics, tissue space fillers, and/or anti-adhesive agents. Also provided are pharmaceutical compositions comprising the inventive polymers and methods of using them including, for example, in the treatment of arthritic and sport-injured knee joints; in reconstruction or cosmetic procedures, intervertebral disc repair, treatment of vocal cord problems, treatment of urinary incontinence, and prevention of adhesion formation following abdominal or gynecological surgery.

31 Claims, 8 Drawing Sheets

OTHER PUBLICATIONS

Craymer et al., Polymer Preprints, 2005, 46(2): 884-885.

Ladmiral et al., European Polymer J, 2004, 40(3):431-449.

Nomura et al., Macromolecules, 1996, 29(2): 540-545.

Supplementary European Search Report for EP 07 77 7140.0 (date of completion Mar. 16, 2010).

Walsh et al., Abstracts of Papers: Part 2: 220$^{th}$ ACS Nat. Meeting, 2000, POLY-319.

Bertin et al., "Indomethacin-Containing Nanoparticles Derived from Amphiphilic Polynorbornene: A Model ROMP-Based Drug Encapsulation System," *Macromolecules*, 37: 8364-8372, 2004.

Maynard et al., "Inhibition of Cell Adhesion to Fibronectin by Oligopeptide-Substituted Polynorbornenes," *J. Am. Chem. Soc.*, 123: 1275-1279, 2001.

Ogawa et al., "Ring-opening metathesis polymerization of steroid-conjugated norbornenes and gradual release of estrone from a polymer film," *Reactive & Functional Polymers*, 70: 563-571, 2010.

Shanbhag et al., "Ester and Amide Prodrugs of Ibuprofen and Naproxen: Synthesis, Anti-inflammatory Activity, and Gastrointestinal Toxicity," *Journal of Pharm. Sciences*, 81: 149-154, 1992.

Wathier et al., "Acidic Polysaccharide Mimics via Ring-Opening Metathesis Polymerization," *J. Am. Chem. Soc.*, 132: 15887-15889, 2010.

Ladmiral et al., "Synthetic glycopolymers: an overview," European Polymer Journal, 40: 431-449, 2004.

* cited by examiner (a) i)$Ru(PPh_3)_2(Cl)_2(CHPh)$, benzen, $CH_2Cl_2$, 25 °C, 4 h. ii) ethyl vinyl ether.
(b) TEA, TFA, $H_2O_2$, $CH_2Cl_2$, MeOH reflux, 16 h.
(c) MeOH, $H_2O$, NaOH, reflux.
(d) THF, NaOH, 2 days.
(e) $OsO_4$, NMO, $H_2O$, 16 h.

| Polymer | $M_w$ | Monomer/Catalyst ratio | PDI | Contact Angle |
|---|---|---|---|---|
| 2 | 187,600<br>350,000<br>500,000<br>10,000,000 | 1,100<br>2,100<br>3,000<br>60,000 | 1.09<br>1.1<br>1.1<br>1.2 | 57-65 |
| 3 | 158,700<br>350,000<br>500,000<br>10,000,000 | | 1.09<br>1.1<br>1.1<br>1.2 | 30-40 |
| 4 | 158,700<br>350,000<br>500,000<br>10,000,000 | | 1.2<br>1.1<br>1.1<br>1.2 | 9-12 |
| 6 | 58,200<br>350,000<br>500,000<br>3,500,000 | 380<br>2300<br>3200<br>22700 | 1.1<br>1.2<br>1.3<br>1.5 | 46-56 |
| 7 | 50,200<br>340,000<br>500,000<br>3,500,000 | | 1.1<br>1.2<br>1.3<br>1.5 | 20-25 |
| 8 | 52,200<br>350,000<br>500,000<br>3,500,000 | | 1.1<br>1.2<br>1.2<br>1.6 | 12-15 |
| 9 | 52,200<br>350,000<br>500,000<br>3,400,000 | | 1.1<br>1.2<br>1.2<br>1.6 | 10-15 |
| 10 | 158,700<br>350,000<br>500,000 | | 1.2<br>1.2<br>1.3 | 30-40 |

FIG. 3

HYDROPHILIC POLYMERS AS MEDICAL LUBRICANTS AND GELS

RELATED APPLICATIONS

The present application is a national phase application under 35 U.S.C. §371 of PCT International Application No. PCT/US2007/011888, filed May 18, 2007, which claims priority under 35 U.S.C. §119(e) to U.S. provisional patent application, U.S. Ser. No. 60/801,751, filed May 19, 2006. The entire contents of each of these priority applications is incorporated herein by reference.

BACKGROUND OF THE INVENTION

Osteoarthritis (OA), a non-inflammatory joint disease characterized by degeneration of joint cartilage, can affect one or more parts of the body, including hands and weight-bearing joints such as knees, hips, feet and the spine. When healthy, cartilage allows bones to glide over each other and has a shock absorber function. In osteoarthritis, the cartilage's surface layer breaks down and wears away, which allows the bones under the cartilage to rub together, causing the common OA symptoms of pain, swelling, and loss of motion of the joint. Furthermore, in joints such as the knees, osteoarthritis is often accompanied by loss of viscosity of the synovial fluid, a thick, gel-like substance that cushions the joint and provides lubrication to reduce friction of the bones.

Osteoarthritis is mainly associated with ageing, with a prevalence of approximately 80% in individuals over 65. Despite being a condition that causes most problems to populations after retirement age, osteoarthritis is also rated the highest cause of work loss in the U.S. and Europe. In addition to age, risk factors known to be associated with osteoarthritis include obesity, traumatic injury and overuse due to sports and occupational stresses.

There is currently no cure for osteoarthritis, and available arthritis therapies are directed at the symptomatic relief of pain, and at improving, or at least maintaining, joint function. Generally, pain relievers such as non-steroidal anti-inflammatory drugs (NSAIDs) or COX-2 inhibitors are used, along with physical therapy. However, in the context of the recent withdrawals of COX-2 inhibitors, physicians are even more limited in their choice of treatment for osteoarthritis.

Viscosupplementation, a procedure involving the injection of gel-like substances (generally hyaluronates or called hyaluronic acid) into a joint to supplement the viscous properties of synovial fluid, has been shown to relieve pain in many osteoarthritis patients who do not get relief from analgesic drugs. The technique has been used in Europe and Asia for several years, but the U.S. Food and Drug Administration did not approve it until 1997. In current procedures of viscosupplementation, hyaluronate preparations are injected to replace or supplement the body's natural hyaluronan, a polysaccharide component of synovial fluid. The injections coat the articular cartilage surface, and thus provide a possible prophylactic barrier for the articular cartilage. However, due to their short lifetime within the joint (about a couple of days), hyaluronate preparations currently available have only limited long-term benefit to the patient and require injection of large quantities of the preparation and/or repeated injections.

Clearly, there is a need for materials with improved performance for use in viscosupplementation for the treatment of osteoarthritis and other conditions affecting weight-bearing joints. In particular, materials with long lifetimes within injected biological fluids or tissues, such as joints, are highly desirable.

SUMMARY OF THE INVENTION

The present invention is directed to biopolymers which mimic the properties of natural polysaccharides found in vivo. The inventive biopolymers, which can be viscous liquids or gels, are potential "bio-lubricants" that can find various applications in the biotechnology, pharmaceutical and medical fields. For example, the biopolymers described herein can be used in viscosupplementation (e.g., in the treatment of osteoarthritic or sport-injured knee joints). They can also be employed as viscoelastics used in cataract surgery, as fillers for cosmetic procedures or treatment of urinary incontinence, and as anti-adhesives for wound care.

More specifically, in one aspect, the present invention provides polymers having one of the following chemical structures:

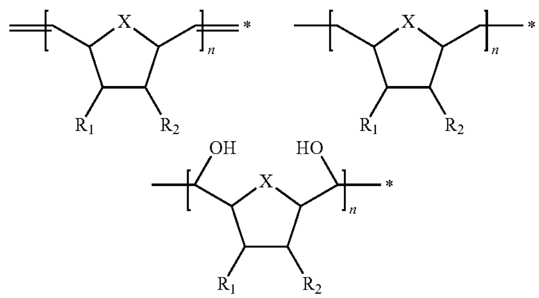

wherein n is an integer from 100 to 200,000;

X is selected from the group consisting of $CH_2$ and O;

$R_1$ and $R_2$ are either the same or different and selected from the group consisting of H, COOR', $COCH_3$, CONHR', OR' and SR', wherein each occurrence of R' is independently selected from the group consisting of H, an alkyl, an alkenyl, an alkynyl, $COCH_3$, $CH_2CH_2OH$, $CH_2CH_2OR''$, an amino acid, a small or large peptide, $COCCH_3{=}CH_2$, $COCH{=}CH_2$, $CH_2CO_2H$, $CH_2CH_2CO_2H$, $CH_2CH_2SH$, $CH_2CH_2SR''$ and $(CH_2CH_2O)_{n'}R'''$, wherein n' is an integer from 1 to 2000;

each occurrence of R" is independently selected from the group consisting of trityl, 4-methyltrityl and 2 pyridyl; and each occurrence of R''' is independently selected from the group consisting of H, an alkyl, an alkenyl, an alkynyl, $COCCH_3{=}CH_2$, $COCH{=}CH_2$, $CH_2CHO$, $CH_2CH_2CHO$, $CO_2H$, $CO_2R''''$, $CH_2CO_2H$, $CH_2CH_2CO_2H$, $CH_2NH_2$, $CH_2NHR''''$, $CH_2N(R'''')_2$, $CH_2CH_2NH_2$, $CH_2CH_2NHR$, $CH_2CH_2N(R'''')_2$, SH, $CH_2CO_2R''''$, and $CH_2CH_2CO_2R''''$, wherein each occurrence of R'''' is independently selected from the group consisting of maleimide, an amino acid, a small or large peptide, phosphate, sulfate, choline, and an activated ester.

In another aspect, the present invention provides polymers having one of the following chemical structures:

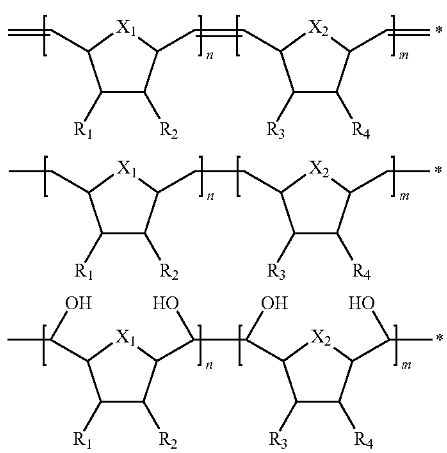
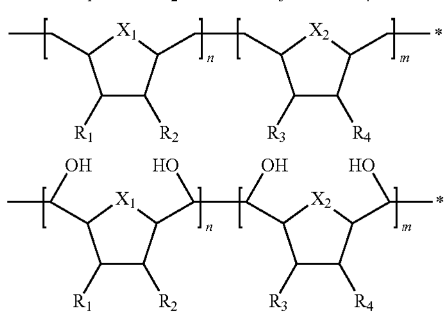

wherein n is an integer from 100 to 200,000 and m is an integer from 100 to 200,000;

$X_1$ and $X_2$ are either the same or different and selected from the group consisting of $CH_2$ and O;

$R_1$, $R_2$, $R_3$ and $R_4$ are either the same or different and selected from the group consisting of H, COOR', $COCH_3$, CONHR', OR' and SR', wherein each occurrence of R' is independently selected from the group consisting of H, an alkyl, an alkenyl, an alkynyl, $COCH_3$, $CH_2CH_2OH$, $CH_2CH_2OR''$, an amino acid, a small or large peptide, $COCCH_3{=}CH_2$, $COCH{=}CH_2$, $CH_2CO_2H$, $CH_2CH_2CO_2H$, $CH_2CH_2SH$, $CH_2CH_2SR''$ and $(CH_2CH_2O)_{n'}R'''$, wherein n' is an integer from 1 to 2000;

each occurrence of R" is independently selected from the group consisting of trityl, 4-methyltrityl and 2 pyridyl; and each occurrence of R" is independently selected from the group consisting of H, an alkyl, an alkenyl, an alkynyl, $COCCH_3{=}CH_2$, $COCH{=}CH_2$, $CH_2CHO$, $CH_2CH_2CHO$, $CO_2H$, $CO_2R''''$, $CH_2CO_2H$, $CH_2CH_2CO_2H$, $CH_2NH_2$, $CH_2NHR''''$, $CH_2N(R'''')_2$, $CH_2CH_2NH_2$, $CH_2CH_2NHR$, $CH_2CH_2N(R'''')_2$, SH, $CH_2CO_2R''''$, and $CH_2CH_2CO_2R''''$, wherein each occurrence of R"" is independently selected from the group consisting of maleimide, an amino acid, a small or large peptide, phosphate, sulfate, choline, and an activated ester.

In another aspect, the present invention provides polymers having one of the following chemical structures:

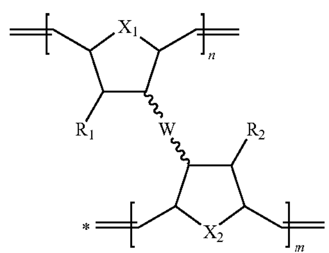

-continued

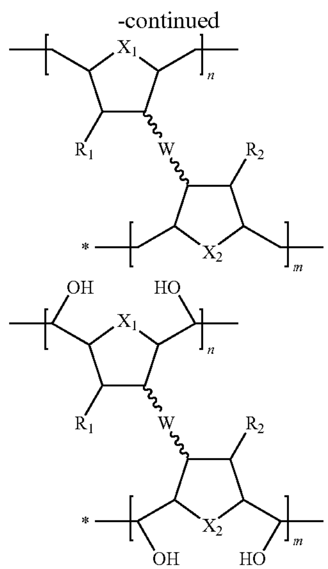
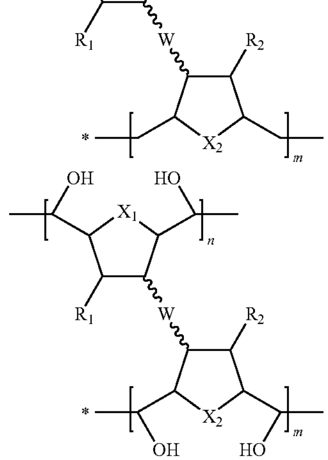

wherein n is an integer from 100 to 200,000 and m is an integer from 100 to 200,000;

$X_1$ and $X_2$ are either the same or different and selected from the group consisting of $CH_2$ and O;

$R_1$ and $R_2$ are either the same or different and selected from the group consisting of H, COOR', $COCH_3$, CONHR', OR' and SR', wherein each occurrence of R' is independently selected from the group consisting of H, an alkyl, an alkenyl, an alkynyl, $COCH_3$, $CH_2CH_2OH$, $CH_2CH_2OR''$, an amino acid, a small or large peptide, $COCCH_3{=}CH_2$, $COCH{=}CH_2$, $CH_2CO_2H$, $CH_2CH_2CO_2H$, $CH_2CH_2SH$, $CH_2CH_2SR''$ and $(CH_2CH_2O)_{n'}R'''$, wherein n' is an integer from 1 to 2000;

each occurrence of R" is independently selected from the group consisting of trityl, 4-methyltrityl and 2 pyridyl; and each occurrence of R''' is independently selected from the group consisting of H, an alkyl, an alkenyl, an alkynyl, $COCCH_3{=}CH_2$, $COCH{=}CH_2$, $CH_2CHO$, $CH_2CH_2CHO$, $CO_2H$, $CO_2R''''$, $CH_2CO_2H$, $CH_2CH_2CO_2H$, $CH_2NH_2$, $CH_2NHR''''$, $CH_2N(R'''')_2$, $CH_2CH_2NH_2$, $CH_2CH_2NHR$, $CH_2CH_2N(R'''')_2$, SH, $CH_2CO_2R''''$, and $CH_2CH_2CO_2R''''$, wherein each occurrence of R"" is independently selected from the group consisting of maleimide, an amino acid, a small or large peptide, phosphate, sulfate, choline, and an activated ester, and W is a linking moiety.

In certain embodiments, the linking moiety comprises a covalent linkage bond. For example, W may comprise a covalent linkage bond selected from the group consisting of ester bond, amide bond, carbamate bond, carbonate bond, ether bond, urethane bond, thiolcarbonate bond, thiourethane bond, shift base bond, peptide ligation, and carbon-carbon bond.

In other embodiments, the linking moiety comprises a non-covalent linkage bond. For example, W may be selected from the group consisting of ionic bond, metal ligand bond, metal chelation bond, hydrogen bond, hydrophobic bond, fluorophobic bond, and van der Waals bond.

In yet other embodiments, the linking moiety comprises a connecting molecule. For example, the connecting molecule may be selected from the group consisting of substituted or unsubstituted polyethylene glycol, polyacrylic glycol and natural polysaccharides. Substituents may be selected from the group consisting of maleimide, activated ester, carboxylic acid, amine, thiol, cysteine, amino acid, acrylate, methacrylate, ester aldehyde, and aldehyde.

In another aspect, the present invention provides polymers having one of the following chemical structures:

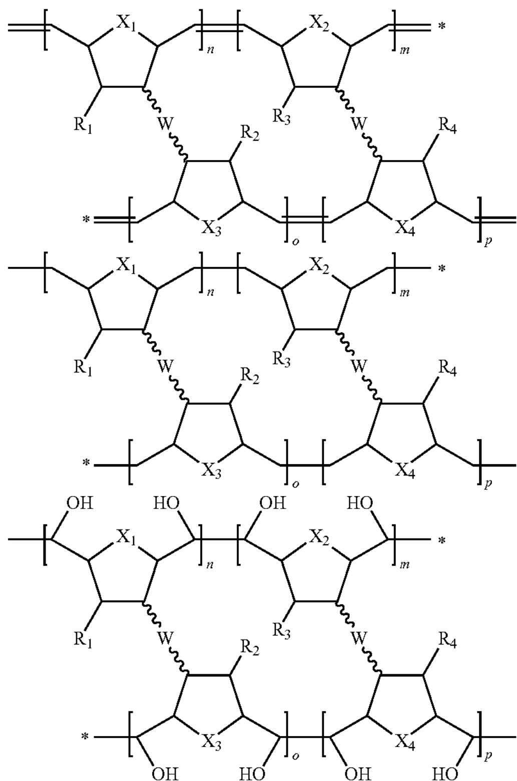

wherein n, m, o and p are either the same or different and each of n, m, o and p is an integer from 100 to 200,000;

$X_1$, $X_2$, $X_3$ and $X_4$ are either the same or different and selected from the group consisting of $CH_2$ and O;

$R_1$, $R_2$, $R_3$ and $R_4$ are either the same or different and selected from the group consisting of H, COOR', $COCH_3$, CONHR', OR' and SR', wherein each occurrence of R' is independently selected from the group consisting of H, an alkyl, an alkenyl, an alkynyl, $COCH_3$, $CH_2CH_2OH$, $CH_2CH_2OR''$, an amino acid, a small or large peptide, $COCCH_3{=}CH_2$, $COCH{=}CH_2$, $CH_2CO_2H$, $CH_2CH_2CO_2H$, $CH_2CH_2SH$, $CH_2CH_2SR''$ and $(CH_2CH_2O)_{n'}R'''$, wherein n' is an integer from 1 to 2000;

each occurrence of R'' is independently selected from the group consisting of trityl, 4-methyltrityl and 2 pyridyl; and each occurrence of R''' is independently selected from the group consisting of H, an alkyl, an alkenyl, an alkynyl, $COCCH_3{=}CH_2$, $COCH{=}CH_2$, $CH_2CHO$, $CH_2CH_2CHO$, $CO_2H$, $CO_2R''''$, $CH_2CO_2H$, $CH_2CH_2CO_2H$, $CH_2NH_2$, $CH_2NHR''''$, $CH_2N(R'''')_2$, $CH_2CH_2NH_2$, $CH_2CH_2NHR$, $CH_2CH_2N(R'''')_2$, SH, $CH_2CO_2R''''$, and $CH_2CH_2CO_2R''''$, wherein each occurrence of R'''' is independently selected from the group consisting of maleimide, an amino acid, a small or large peptide, phosphate, sulfate, choline, and an activated ester, and W is a linking moiety.

In certain embodiments, the linking moiety comprises a covalent linkage bond. For example, W may comprise a covalent linkage bond selected from the group consisting of ester bond, amide bond, carbamate bond, carbonate bond, ether bond, urethane bond, thiolcarbonate bond, thiourethane bond, shift base bond, peptide ligation, and carbon-carbon bond.

In other embodiments, the linking moiety comprises a non-covalent linkage bond. For example, W may be selected from the group consisting of ionic bond, metal ligand bond, metal chelation bond, hydrogen bond, hydrophobic bond, fluorophobic bond, and van der Waals bond.

In yet other embodiments, the linking moiety comprises a connecting molecule. For example, the connecting molecule may be selected from the group consisting of substituted or unsubstituted polyethylene glycol, polyacrylic glycol and natural polysaccharides. Substituents may be selected from the group consisting of maleimide, activated ester, carboxylic acid, amine, thiol, cysteine, amino acid, acrylate, methacrylate, ester aldehyde, and aldehyde.

In another aspect, the present invention provides pharmaceutical compositions comprising at least one pharmaceutically acceptable carrier and an effective amount of at least one inventive polymer described above.

In another aspect, the present invention provides a method of treating a diseased or injured synovial joint in a subject, the method comprising injecting an effective amount of an inventive polymer. In certain embodiments, injecting an effective amount of an inventive polymer comprises performing a single injection. In other embodiments, injecting an effective amount of an inventive polymer comprises performing at least two injections at different time points. Diseased or injured synovial joints that can be treated using this inventive method include osteoarthritic joints and sport-injured joints, such as joints of the knee, hip, elbow, ankle, and wrist.

In another aspect, the present invention provides a method of repairing skin in a subject, the method comprising administering to the subject an effective amount of an inventive polymer. In certain embodiments, the polymer is injected to the area of skin to be repaired. In other embodiments, the polymer is topically applied to the area of skin to be repaired.

In still another aspect, the present invention provides a method of repairing an intervertebral disc in a subject, the method comprising administering to the subject an effective amount of an inventive polymer. For example, the polymer may be injected to the intervertebral disc to be repaired.

In yet another aspect, the present invention provides a method of treating urinary incontinence in a subject, the method comprising administering to the subject an effective amount of an inventive polymer. The polymer may be injected to at least one defective area of the subject's urinary system.

In the methods of treatment of the invention, the polymer may be used as a viscous liquid or as a gel and may further comprise an additional substance, for example, a substance to be delivered to the area of administration of the polymer (e.g., joint, skin, intervertebral disc, urinary system). The additional substance may be one or more of a growth factor, a cytokine, a small molecule, an analgesic, an anesthetic, an antimicrobial agent, an antibacterial agent, an antiviral agent, an antifungal agent, an antibiotic, an anti-inflammatory agent, an antioxidant, and an antiseptic agent.

BRIEF DESCRIPTION OF THE DRAWING

FIG. 3 lists SEC and contact angle data obtained for some of the inventive polymers.

DEFINITIONS

Figure 1:
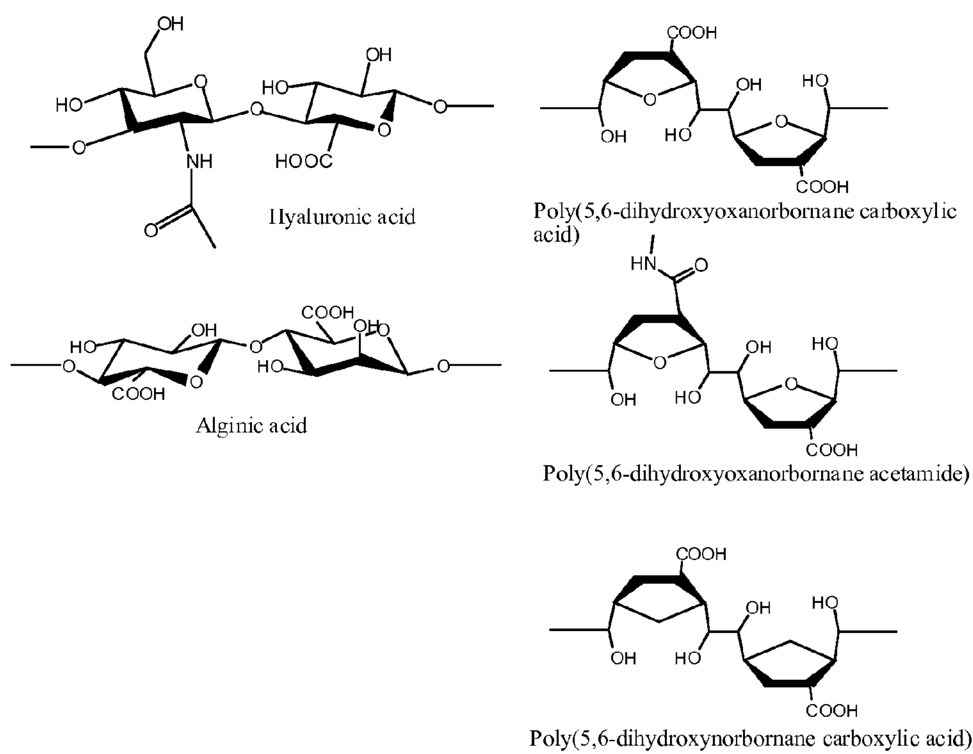
FIG. 1 presents the chemical structures of alginic acid, hyaluronic acid and examples of polysaccharide mimics of the invention.

Throughout the specification, several terms are employed that are defined in the following paragraphs.

The terms "individual" and "subject" are used herein interchangeably. They refer to a human or another mammal (e.g., primates, dogs, cats, goats, horses, pigs, mice, rabbits, and the like). In certain preferred embodiments, the subject is human. The terms do not denote a particular age, and thus encompass adults, children, and newborn.

The term "treatment" is used herein to characterize a method or process that is aimed at (1) delaying or preventing the onset of a disease or condition; (2) slowing down or stopping the progression, aggravation, or deterioration of the symptoms of the disease or condition; (3) bringing about ameliorations of the symptoms of the disease or condition; or (4) curing the disease or condition. A treatment may be administered prior to the onset of the disease, for a prophylactic or preventive action. Alternatively or additionally, the treatment may be administered after initiation of the disease or condition, for a therapeutic action.

The term "local", when used herein to characterize the delivery, administration or application of a polymer of the present invention, or a pharmaceutical composition thereof, is meant to specify that the polymer or composition, is delivered, administered or applied directly to the site to be treated or in the vicinity of the site to be treated for a localized effect. For example, an inventive polysaccharide mimic used as a viscosupplement will generally be injected directly to an osteoarthritic knee joint; an inventive polysaccharide mimic used as tissue space filler will generally be injected directly to a diseased or damaged vocal cord, or to a skin area displaying lines or wrinkles. Preferably, local administration is effected without any significant absorption of components of the polysaccharide mimic into the patient's blood stream (to avoid a systemic effect).

A "pharmaceutical composition" is defined herein as comprising an effective amount of at least one active ingredient (e.g., an inventive polysaccharide mimic), and at least one pharmaceutically acceptable carrier.

As used herein, the term "pharmaceutically acceptable carrier" refers to a carrier medium which does not interfere with the effectiveness of the biological activity of the active ingredient(s) and which is not excessively toxic to the host at the concentration at which it is administered. The term includes solvents, dispersion media, coatings, antibacterial and antifungal agents, isotonic agents, absorption delaying agents, and the like. The use of such media and agents for pharmaceutically active substances is well known in the art (see for example, *"Remington's Pharmaceutical Sciences"*, E. W. Martin, 18$^{th}$ Ed., 1990, Mack Publishing Co.: Easton, Pa., which is incorporated herein by reference in its entirety).

As used herein, the term "effective amount" refers to any amount of a molecule, compound or composition that is sufficient to fulfill its intended purpose(s), i.e., to elicit a desired biological or medicinal response in a tissue or subject. Examples of intended purposes of an inventive polymer include, but are not limited to, to provide viscosupplementation to a joint, to allow soft tissue augmentation, to prevent or reduce adhesion formation, to facilitate tissue manipulation, and/or to maintain, support or protect soft tissue.

As used herein, the term "soft tissue augmentation" include, but is not limited to, dermal tissue augmentation; filling of lines, folds, wrinkles, minor facial depressions, cleft lips and the like, especially in the face and neck; correction of minor deformities due to aging, disease, including in the hands and feet, fingers and toes; augmentation of the vocal cords or glottis to rehabilitate speech; dermal filling of sleep lines and expression lines; replacement of dermal and subcutaneous tissue lost due to aging; lip augmentation; filling of crow's feet and the orbital groove around the eye; breast augmentation; chin augmentation; augmentation of the cheek and/or nose; filling of indentations in the soft tissue, dermal or subcutaneous, due to, e.g., overzealous liposuction or other trauma; filling of acne or traumatic scars and rhytids; filling of nasolabial lines, nasoglobellar lines and infraoral lines.

As used herein, the term "soft tissue" includes all tissue of the body except bone. Examples of soft tissue include, but are not limited to, muscles, tendons, fibrous tissues, fat, blood vessels, nerves, and synovial tissues.

The terms "bioactive agent" and "biologically active agent" are used herein interchangeably. They refer to compounds or entities that alter, inhibit, activate or otherwise affect biological or chemical events. For example, bioactive agents may include, but are not limited to, vitamins, anticancer substances, antibiotics, immunosuppressants, anti-viral substances, enzyme inhibitors, opioids, hypnotics, lubricants, tranquilizers, anti-convulsants, muscle relaxants, antispasmodics and muscle contractants, anti-glaucoma compounds, modulators of cell-extracellular matrix interactions including cell growth inhibitors and anti-adhesion molecules, vasodilating agents, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents. A more complete, although not exhaustive, listing of classes and specific drugs suitable for use in the present invention may be found in *"Pharmaceutical Substances: Synthesis, Patents, Applications"* by A. Kleeman and J. Engel, Thieme Medical Publishing, 1999; and the *"Merck Index: An Encyclopedia of Chemicals, Drugs, and Biologicals"*, S. Budavari et al. (Eds), CRC Press, 1996, both of which are incorporated herein by reference.

The term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. Typically, small molecules have a molecular weight of less than about 1,500 Da. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§330.5, 331 through 361, and 440 through 460; drugs for veterinary use listed by the FDA under 21 C.F.R. §§500 through 589, incorporated herein by reference, are all considered suitable for use with the present polysaccharide mimic polymers.

The terms "polysaccharide", "carbohydrate", and "oligosaccharide" are used herein interchangeably. They refer to a compound that comprises at least two sugar units, or derivatives thereof. Polysaccharides may be purified from natural sources such as plants or may be synthesized de novo in the laboratory. Polysaccharides isolated from natural sources may be modified chemically to change their chemical or physical properties (e.g., reduced, oxidized, phosphorylated, cross-linked). Carbohydrate polymers or oligomers may include natural sugars (e.g., glucose, fructose, galactose, mannose, arabinose, ribose, xylose, etc.) and/or modified sugars (e.g., 2'-fluororibose, 2'-deoxyribose, etc.). Polysaccharides may also be either straight or branched. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, poly (dextrose), and fructose. Glycosaminoglycans are also considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

An entity is herein said to be "associated with" another entity if they are linked by a direct or indirect, covalent or non-covalent interaction. In certain embodiments, the association is covalent. Desirable non-covalent interactions include hydrogen bonding, van der Walls interactions, hydrophobic interactions, magnetic interactions, electrostatic interactions, or combinations thereof.

In general, the term "aliphatic", as used herein, includes both saturated and unsaturated, straight chain (i.e., unbranched) or branched aliphatic hydrocarbons, which are optionally substituted with one or more functional groups, as defined below. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms.

Illustrative aliphatic groups thus include, but are not limited to, for example, methyl, ethyl, n-propyl, isopropyl, allyl, n-butyl, sec-butyl, isobutyl, tert-butyl, n-pentyl; sec-pentyl, isopentyl, tert-pentyl, n-hexyl, sec-hexyl, moieties and the like, which again, may bear one or more substituents, as previously defined. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups, as defined below. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$-cyclohexyl, cyclohexenylethyl, cyclohexanylethyl, norborbyl moieties and the like, which again, may bear one or more substituents.

The term "heteroaliphatic", as used herein, refers to aliphatic moieties in which one or more carbon atoms in the main chain have been substituted with an heteroatom. Thus, a heteroaliphatic group refers to an aliphatic chain which contains one or more oxygen sulfur, nitrogen, phosphorus or silicon atoms, e.g., in place of carbon atoms. Heteroaliphatic moieties may be saturated or unsaturated, branched or linear (i.e., unbranched), and substituted or unsubstituted. Substituents include, but are not limited to, any of the substituents mentioned below, i.e., the substituents recited below resulting in the formation of a stable compound.

The term "heteroalicyclic", as used herein, refers to compounds which combine the properties of heteroaliphatic and the cyclic compounds and include but are not limited to saturated and unsaturated mono- or polycyclic heterocycles such as morpholino, pyrrolidinyl, furanyl, thiofuranyl, pyrrolyl, etc, which are optionally substituted with one or more functional groups. Substituents include, but are not limited to, any of the substituents mentioned below, i.e., the substituents recited below resulting in the formation of a stable compound.

The term "alkyl", as used herein, refers to saturated, straight- or branched-chain hydrocarbon radicals derived from a hydrocarbon moiety containing between one and twenty carbon atoms by removal of a single hydrogen atom, which alkyl groups are optionally substituted with one or more functional groups. Substituents include, but are not limited to, any of the substituents mentioned below, i.e., the substituents recited below resulting in the formation of a stable compound. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

The term "alkoxy", as used herein, refers to an alkyl group, as previously defined, attached to the parent molecular moiety through an oxygen atom. Examples include, but are not limited to, methoxy, ethoxy, propoxy, isopropoxy, n-butoxy, tert-butoxy, neopentoxy, and n-hexoxy.

The term "alkenyl" denotes a monovalent group derived from a hydrocarbon moiety having at least one carbon-carbon double bond, which alkenyl group is optionally is substituted with one or more functional groups. In certain embodiments, an alkenyl group contains between one and twenty carbon atoms. Substituents include, but are not limited to, any of the substituents mentioned below, i.e., the substituents recited below resulting in the formation of a stable compound. Alkenyl groups include, for example, ethenyl, propenyl, butenyl, 1-methyl-2-buten-1-yl, and the like.

The term "alkynyl", as used herein, refers to a monovalent group derived from a hydrocarbon having at least one carbon-carbon triple bond, which alkynyl group is optionally substituted. In certain embodiments, an alkynyl group contains between one and twenty carbon atoms. Substituents include, but are not limited to, any of the substituents mentioned below, i.e., the substituents recited below resulting in the formation of a stable compound. Representative alkynyl groups include ethynyl, 2-propynyl (propargyl), 1-propynyl, and the like.

The term "amine", as used herein, refers to one, two, or three alkyl groups, as previously defined, attached to the parent molecular moiety through a nitrogen atom. The term "alkylamino" refers to a group having the structure —NHR' wherein R' is an alkyl group, as previously defined; and the term "dialkylamino" refers to a group having the structure —NR'R", wherein R' and R" are each independently selected from the group consisting of alkyl groups. The term "trialkylamino" refers to a group having the structure —NR'R"R'", wherein R', R", and R'" are each independently selected from the group consisting of alkyl groups. Additionally, R', R", and/or R'" taken together may optionally be $—(CH_2)_k—$ where k is an integer from 2 to 6. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "aryl", as used herein, refers to stable mono- or polycyclic, unsaturated moieties having preferably 3-14 carbon atoms, each of which may be substituted or unsubstituted. Substituents include, but are not limited to, any of the substituents mentioned below, i.e., the substituents recited below resulting in the formation of a stable compound. The term aryl may refer to a mono- or bicyclic carbocyclic ring system having one or two aromatic rings including, but not limited to, phenyl, naphthyl, tetrahydronaphthyl, indanyl, indenyl and the like.

The term "heteroaryl", as used herein refers to a stable heterocyclic or polyheterocyclic, unsaturated radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms. Heteroaryl moieties may be substituted or unsubstituted. Substituents include, but are not limited to, any of the substituents mentioned below, i.e., the substituents recited below resulting in the formation of a stable compound. Examples of heteroaryl nuclei include pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein, may be attached via an aliphatic, alicyclic, heteroaliphatic, heteroalicyclic, alkyl or heteroalkyl moiety and thus also include -aliphatic)aryl, -(heteroaliphatic)aryl, -(aliphatic)heteroaryl, -(heteroa-liphatic)heteroaryl, -alkyl) aryl, -(heteroalkyl)aryl, -(heteroalkyl)aryl, and -heteroalkyl)-heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, -(heteroaliphatic) heteroaryl, -(alkyl)aryl, -(heteroalkyl)aryl, -(heteroalkyl) aryl, and -(heteroalkyl)heteroaryl" are interchangeable.

The term "carboxylic acid", as used herein, refers to a group of formula $—CO_2H$.

The terms "halo", "halide", and "halogen", as used herein, refers to an atom selected from fluorine, chlorine, bromine, and iodine.

The term "methylol", as used herein, refers to an alcohol group of structure $—CH_2OH$.

The term "hydroxyalkyl" refers to an alkyl group, as defined above, bearing at least one OH group.

The term "mercaptoalkyl", a used herein, refers to an alkyl group, as defined above, bearing at least one SH group.

The term "heterocyclic", as used herein, refers to a non-aromatic partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. Heterocyclic moieties may be substituted or unsubstituted. Substituents include, but are not limited to, any of the substituents mentioned below, i.e., the substituents recited below resulting in the formation of a stable compound. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized.

The term "acyl", as used herein, refers to a group comprising a carbonyl group of the formula C═O. Examples of acyl groups include aldehydes, ketones, carboxylic acids, acyl halides, anhydrides, thioesters, amides, urea, carbamate, and carboxylic esters.

The term "hydrocarbon", as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions. Likewise, the term "fluorocarbon", as used herein, refers to any chemical group comprising more fluorine atoms than hydrogen atoms attached to carbons. The fluorocarbon may be substituted or unsubstituted. A fluorocarbon may be saturated, unsaturated, branched, unbranched, cyclic, polycyclic or heterocyclic.

The term "substituted", whether preceded by the term "optionally" or not, refers to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Examples of substituents include, but are not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; $—NO_2$; —CN; —NCO; $—CF_3$; $—CH_2CF_3$; $—CHCl_2$; $—CH_2OR_x$; $—CH_2CH_2OR_x$; $—CH_2N(R_x)_2$; $—CH_2SO_2CH_3$; $—C(O)R_x$;

—$CO_2(R_x)$; —$CON(R_x)_2$; —$OC(O)R_x$; —$C(O)OC(O)R_x$; —$OCO_2R_x$; —$OCON(R_x)_2$; —$N(R_x)_2$; —$S(O)_2R_x$; —$OCO_2R_x$; —$NR_x(CO)R_x$; —$NR_x(CO)N(R_x)_2$, wherein each occurrence of $R_x$ independently includes, but is not limited to, H, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

DETAILED DESCRIPTION OF CERTAIN PREFERRED EMBODIMENTS

The present invention is directed to new biopolymers which mimic the properties of natural polysaccharides found in vivo. The inventive biopolymers, which can be viscous liquids or gels, are potential "bio-lubricants" that can find various applications in the biotechnology, pharmaceutical and medical fields.

I. Polysaccharide Substitutes

Polysaccharides are ubiquitous in nature and are of widespread use in the biotechnology, food, and pharmaceutical industries. The biological roles of polysaccharides are diverse and include energy storage and generation in plants (amylose, amylopectin) and animals (glycogen), structural materials in plants (cellulose, alginate) and exoskeletons of insects and arthropods (chitin), cellular recognition and signaling actuators (glycosaminoglycans, heparin, antigens) and dynamic lubricating components of the mammalian extracellular matrix (hyaluronan, proteoglycans) (P. M. Collins, *"Carbohydrates"*, Chapman and Hall: New York, N.Y., 1987; H. S. El Khadem, *"Carbohydrate Chemistry"*, Academic Press: Orlando, Fla., 1988; R. A. Dwek et al., Ann. Rev. Biochem., 1993, 62: 65-100; L. A. Lasky, Science, 1992, 258: 964-969; N. Sharon, Sci. Amer., 1980, 254: 90-116; N. Sharon and H. L is, Science, 1989, 246: 227-234; V. Ginsburg and P. Robbins, *"Biology of Carbohydrates—Vols. I-III"*, Wiley: New York, N.Y., 1981; J. Preiss, *"The Biochemistry of Plants Vol. 3. Carbohydrates: Structure and Function"*, Academic Press: New York, N.Y., 1980; W. I. Weiss et al., Nature, 1992, 360: 127-134; L. Kjellen et al., Ann. Rev. Biochem., 1991, 60: 443-475). The specific combinations of macromolecular mechanical properties and discreet chemical functionalities (carboxylic acids, amides, sulfonates, etc) of the polysaccharide allow for these numerous biological roles.

The present invention relates to the synthesis of polymers that mimic the macromolecular properties of polysaccharides while being amenable to chemical derivatization. This approach is aimed at further understanding the relationship between molecular structure, physical properties, and biological function as well as at providing a new class of synthetic polymer substitutes for the numerous industrial and pharmaceutical applications of acidic polysaccharides.

Most polysaccharides possess repeating puranase structures joined by an ether linkage with the simple stoichiometric formula $(CH_2O)_n$. The acidic polysaccharides were identified as the first case study since they are widely found in both plants and microbiologic organisms. Thus, the synthesis and physical properties of novel polymers, which are synthetic analogs of natural acidic polysaccharides, hyaluronates, and derivatives thereof, are reported herein.

Preparation of Polysaccharide Substitutes

As shown in FIG. 1, the acidic polysaccharide, alginic acid, is a linear block polymer of 1-4 linked β-D-mannuronic acid and α-L-guluronic acid. Sodium alginate is of commercial value in the biotechnology (cell encapsulation), food (thickeners), and pharmaceutical (formulations) industries. The initial effort by the present Applicants was to reproduce this basic macromolecular structure of a repeating cyclic structure containing two secondary alcohols and a carboxylic acid. The hydrophilic polymers, poly(5,6-dihydroxynorbornane carboxylic acid) and poly(5,6-dihydroxyoxanorbornane carboxylic acid), possess these basic characteristics (see FIG. 1).

An efficient and general synthetic strategy to synthesize novel hydrophilic polymers bearing carboxylic acids pendent groups (and derivatives thereof) is described herein. For example, the polymers poly(5,6-dihydroxynorbornane carboxylic acid) and poly(5,6-dihydroxyoxanorbornane carboxylic acid) were prepared by ROMP (ring-opening metathesis polymerization) of the appropriate strained olefin in the presence of Grubbs' catalyst and subsequently modified to tune their hydrophobic/hydrophilic properties.

Figure 2:
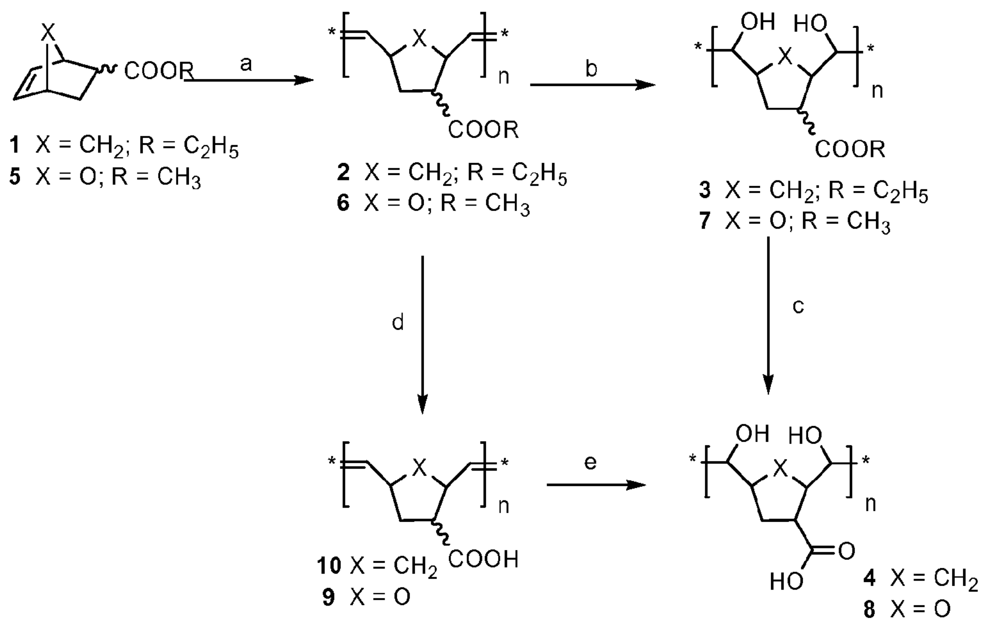
FIG. 2 is a scheme showing an example of a synthesis of polysaccharide mimics according to the present invention.

More specifically, as shown in FIG. 2, poly(5,6-dihydroxynorbornane carboxylic acid) and poly(5,6-dihydroxyoxanorbornane carboxylic acid) were synthesized via ROMP of a cyclic olefin followed by dihydroxylation of the double-bond. The monomer, either ethyl-5-norbornen-2-carboxylate (1) or methyl-5-norbornene-2-carboxylate (5) was dissolved in benzene:dichloromethane (8:1), and polymerized using Grubbs' catalyst, bis-tricyclohexyl-phosphine)benzylidine ruthenium (IV) dichloride (B. M. Novak and R. H. Grubbs, J. Am. Chem. Soc., 1988, 110: 960-961; P. Schwab et al., J. Am. Chem. Soc., 1996, 118: 100-110; P. Schwab et al., Angewandte Chemie International Ed. Eng., 1995, 34: 2039-2041; M. R. Buchmeiser et al., J. Am. Chem. Soc., 1997, 119: 9166-9174) at different monomer to catalyst ratio (see Table 1). The polymerization reaction was terminated by addition of ethyl vinyl ether. Integration of the trans vinyl peak at approximately 5.3 ppm and cis vinyl peak at 5.2 ppm for polymers 2 and 6 indicated that the polymers were 87% and 77% trans, respectively, consistent with previous studies using this catalyst. Of importance here is the preparation of large molecular weight polymers which possess desired properties such as high viscosity.

The polymers 2 and 6 were next either dihydroxylated with trifluoroacetic acid and $H_2O_2$ to yield polymers 3 and 7 or saponified with NaOH to yield polymers 9 and 10. For example, polymer 9 had a molecular weight of 3,400,000. Alternatively, the polymers can be hydrogenated to yield the methylene backbone polymers.

For polymers 3 and 7, the olefinic protons were no longer present in the NMR spectrum, and new proton resonances at 3.5-3.6 ppm were observed consistent with their structures. Finally, the esters were hydrolyzed with $K_2CO_3$ in methanol to afford white fibrous polymers 4 and 8 upon freeze drying. Polymers 4 and 8 were not soluble in tetrahydrofuran (THF) but in water, and thus the molecular weights were not determined and compared to polystyrene standards but with dextran standards. GPC analysis revealed a Mn consistent with a polymer that was not degraded during the chemical derivatization procedures.

For polymers 9 and 10, the ester protons were no longer present in the NMR spectrum, and the polymers were found to be water soluble.

These transformations in backbone structure were also monitored by infrared (IR) spectroscopy. The polyolefin 2 and polyolefin 6 were found to possess IR absorptions at 2360 $cm^{-1}$ for the alkene. Subsequent dihydroxylation and/or deesterification of 2 and 6 afforded polymers 4, 8, 9 and 10, respectively and the IR stretches for hydroxyl groups were observed at 3400 $cm^{-1}$.

Polymers 2-4 and 6-10 were found to display a range of physical properties consistent with their chemical composition. Polymers 2 and 6 are soluble in hydrophobic solvents such as benzene, toluene and chloroform ($CHCl_3$). The hydroxylated polymers 3 and 7 are not soluble in hydrophobic solvents and slightly soluble in methanol. The hydrophilic polymers 4, 9 and 10 are slightly soluble in methanol and soluble in water, whereas polymers 8 is soluble only in water.

Figure 4:
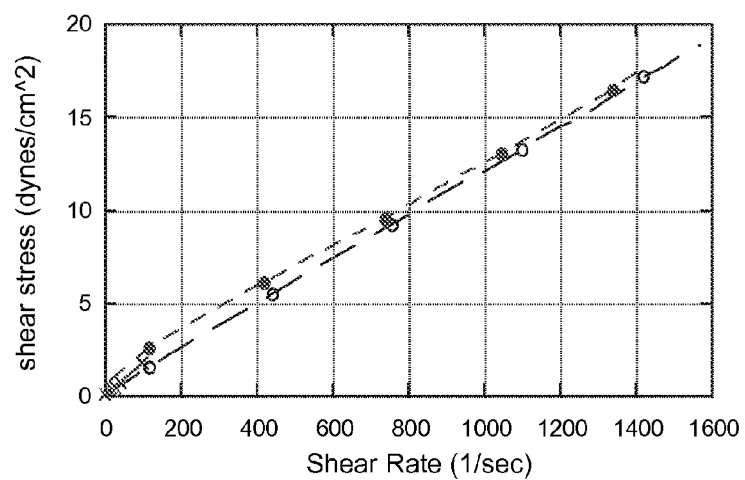
FIG. 4 presents viscosity data for alginic acid, and inventive polymers 4 and 8.
Figure 5:
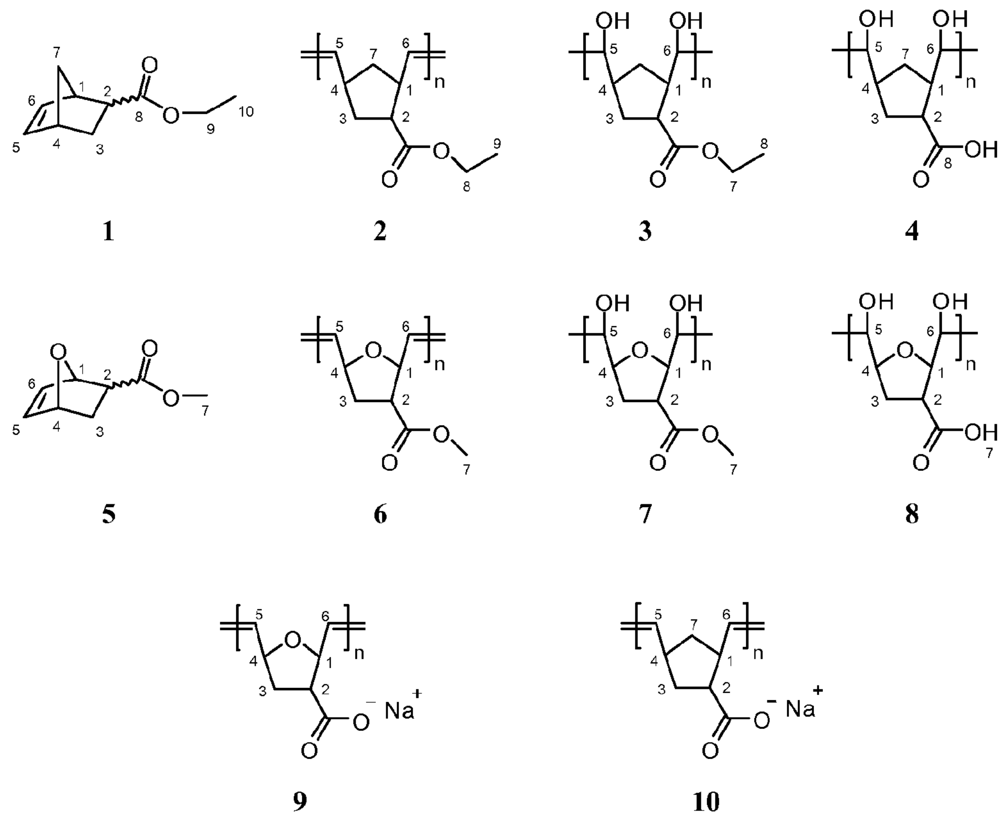
FIG. 5 shows the chemical structures of inventive compounds 1-9.

Contact angle experiments on thin films of these polymers revealed the same trends in hydrophobic/hydrophilic character. The contact angle of polymers 2 and 6 were found to be 57° and 46°, respectively, consistent with a hydrophobic polymer. Introduction of the hydroxyl and carboxyl functional groups to the polymer dramatically lowered the contact intact to 9° and 12° for polymers 4 and 8, respectively and to 10° and 30° for polymers 9 and 10, respectively. For comparison, alginate is soluble only in water and the contact angle of an alginate film is 7°. The hydrophilic polymers 4 and 8 were also found to exhibit Theological properties similar to alginate in aqueous solution, as shown in FIG. 4. Polymers 4 and 8 and alginic acid display Newtonian behavior with a viscosity of 1.06 cp, 1.12 cp and 1.11 cp, respectively (5% w/v solutions).

Figure 6:
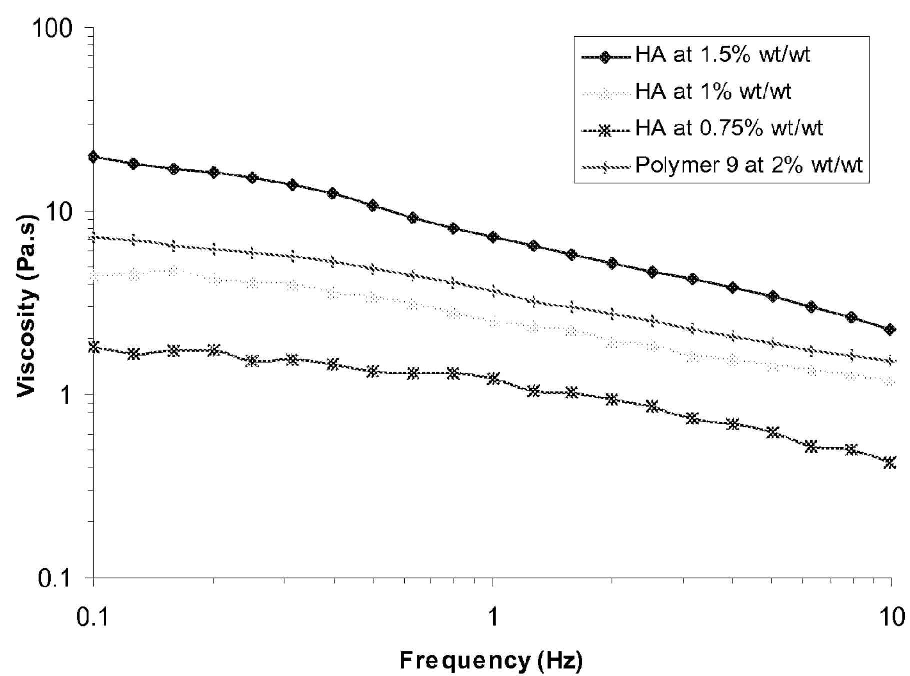
FIG. 6 presents viscosity data for hyaluronic acid and polymer 9.

Rheological experiments (see FIGS. 6 and 7) of these polymers in solution revealed the same trends as natural hyaluronate or hyaluronic acid (HA) with respect to viscosity and coefficient of friction. For example, the viscosity and coefficient of friction of polymer 9 were found to be similar to HA. The viscosity of polymer 9 at 2% and HA at 1.1-% wt/wt are 3.6 Pa·s and 3.5 Pa·s, respectively. The coefficient of friction of polymer 9 at 2% and HA at 1.5% wt/wt are 0.0068 and 0.0076, respectively.

Thus, the present invention provides a facile route to new polymers that includes ROMP of cyclic olefins in the presence of Grubbs' catalyst. The synthetic protocol provided herein is an attractive route to novel polymers (in particular hydrophilic polymers), which possesses the following advantages: (1) a living polymerization reaction, (2) controlled molecular weight with low PDIs, (3) readily available bicyclic olefin monomers afforded by selection of the appropriate deinophile and diene for monomer preparation, and (4) versatility of the olefin functionality for introduction of specific chemical groups. The procedure described herein expands the synthetic repertoire currently limited to polymerization of anhydrous sugars (M. Okada et al., Makromol. Chem., 1978, 179: 949-958; M. C. Kasuya and K. Hatanaka, Macromolecules, 1999, 32: 2131-2136; T. Yoshida et al., J. Polymer Sci. A: Polymer Chem., 1998, 36: 841-850); carbohydrate-derivatized cyclic olefins (K. H. Mortell et al., J. Am. Chem. Soc., 1994, 116: 12053-12054; C. Fraser and R. H. Grubbs, Macromolecules, 1995, 28: 7248-7255), carbohydrate-derivatized vinyl monomers (J. M. Havard et al., Macromolecules, 1999, 32: 86-94; W. J. Zhou et al., Macromolecules, 1999, 32: 5507-5513) and polycondensation of diamine- and diacid-derivatized carbohydrate monomers (D. E. Kiely et al., J. Am. Chem. Soc., 1994, 116: 571-578).

The polymers synthesized were found to display a range of physical properties, and the tailoring of a specific macromolecular property was demonstrated. The solution behavior of, for example, polymers 4 and 9 was found to resemble that of the acidic polysaccharide, hyaluronic acid or alginic acid, even though these polymers lack the glycosidic bond and pyranose repeating structure. The pendent carboxylic acid functionalities, like in alginic acid, can potentially serve as pH-sensitive responsive elements or ionic cross-linking sites for divalent cations and polycations.

As will be appreciated by one skilled in the art, the synthetic approach described above may be applied to the synthesis of polymers that do not contain carboxylic or ester groups. Thus, the inventive synthetic approach may be used to prepare polymers with any of the following chemical structures:

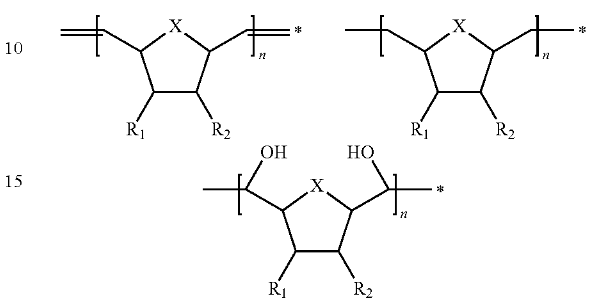

wherein n is an integer from 100 to 200,000;

X is selected from the group consisting of $CH_2$ and O;

$R_1$ and $R_2$ are either the same or different and selected from the group consisting of H, COOR', $COCH_3$, CONHR', OR' and SR', wherein each occurrence of R' is independently selected from the group consisting of H, an alkyl, an alkenyl, an alkynyl, $COCH_3$, $CH_2CH_2OH$, $CH_2CH_2OR''$, an amino acid, a small or large peptide, $COCCH_3{=}CH_2$, $COCH{=}CH_2$, $CH_2CO_2H$, $CH_2CH_2CO_2H$, $CH_2CH_2SH$, $CH_2CH_2SR''$ and $(CH_2CH_2O)_{n'}R'''$, wherein n' is an integer from 1 to 2000;

each occurrence of R'' is independently selected from the group consisting of trityl, 4-methyltrityl and 2 pyridyl; and each occurrence of R''' is independently selected from the group consisting of H, an alkyl, an alkenyl, an alkynyl, $COCCH_3{=}CH_2$, $COCH{=}CH_2$, $CH_2CHO$, $CH_2CH_2CHO$, $CO_2H$, $CO_2R''''$, $CH_2CO_2H$, $CH_2CH_2CO_2H$, $CH_2NH_2$, $CH_2NHR''''$, $CH_2N(R'''')_2$, $CH_2CH_2NH_2$, $CH_2CH_2NHR$, $CH_2CH_2N(R'''')_2$, SH, $CH_2CO_2R''''$, and $CH_2CH_2CO_2R''''$, wherein each occurrence of R'''' is independently selected from the group consisting of maleimide, an amino acid, a small or large peptide, phosphate, sulfate, choline, and an activated ester.

The present invention encompasses any of these polymers. In addition, the present invention provides polymers that can be formed using two or more of the polymers described above. The polymer may result from the formation of a direct or indirect linkage between the two or more polymers. Examples of direct linkages include covalent bonds and non-covalent bonds. Examples of covalent bonds include, but are not limited to, ester bond, ether bond, urea bond, amide bond, carbonate bond, thiocarbonate bond, thiourea bond, carbamate bond, urethane bond, shift base bond, peptide ligation (e.g., thiozolidine, N-thiazolidine), and carbon-carbon bond. Examples of non-covalent bonds include, but are not limited to, ionic bond, metal ligand bond, metal chelation bond (e.g., calcium or barium coordinated by a carboxylic acid), hydrogen bond, hydrophobic bond, fluorophobic bond, and van der Waals bond. Examples of indirect linkages include, but are not limited to, connecting molecules such as polyethylene glycol, polyacrylic glycol and natural polysaccharides, that can optionally be substituted, for example, with maleimide, activated ester, carboxylic acid, amine, thiol, cysteine, amino acid, acrylate, methacrylate, ester aldehyde, or aldehyde groups.

II. Polysaccharide Substitutes as Delivery Agents

The inventive polymers, which can be viscous liquids or gels, can be used as delivery agents. For example, an inventive polymer can be used to deliver one or more substances at the location where the polymer is injected (or applied) (e.g., joint, intervertebral disc, urinary system, skin).

Substances that can be delivered using the inventive polymers include any molecule, agent or compound that is suitable to be delivered to a patient at the location where the inventive polymer is to be injected or applied. For example, a suitable substance may be one or more of a growth factor, a cytokine, a small molecule, an analgesic, an anesthetic, an antimicrobial agent, an antibacterial agent, an antiviral agent, an antifungal agent, an antibiotic, an anti-inflammatory agent, an antioxidant, and an antiseptic agent.

Association between the polymer and substance may be covalent or non-covalent, direct or through a linker (e.g., a bifunctional agent). The association may be achieved by taking advantage of functional groups present on the polymer and substance. As can be readily appreciated by those skilled in the art, a polymer may be associated with any number of substances, which can be identical or different. In certain embodiments, the association between the polymer and substance is such that, in vivo, the substance is released from the polymer.

III. Uses Applications of the Inventive of the Inventive Polysaccharide Substitutes The new polymers disclosed herein can find various applications in the biotechnology, pharmaceutical and medical fields. For example, polymers of the present invention can be used in viscosupplementation, e.g., in the treatment of osteoarthritic or sport-injured knee joints. They can also be used as viscoelastics, for example in ophthalmic surgery, as tissue space filler for cosmetic procedures or treatment of urinary incontinence, and as anti-adhesives for wound care.

Accordingly, the present invention provides methods which generally include administration of an effective amount of an inventive polymer, or a pharmaceutical composition thereof, to an individual in need thereof.

A. Indications

Viscosupplements

Polymers of the present invention can be used as viscosupplements. As already mentioned above, viscosupplementation is a procedure involving injection of gel-like substances (generally hyaluronates, HAs) into a joint to supplement the viscous properties of synovial fluid. HA injections have been found to relieve pain in many osteoarthritis patients, with HAs of higher molecular weights (i.e., higher viscosity) showing better efficacy than those with lower molecular weights (i.e., lower viscosity). However, due to their short lifetime within the joint (about a couple of days), hyaluronate preparations currently available have only limited long-term benefit to the patient and require injection of large quantities of preparation and/or repeated injections.

Viscoelastics

Polymers of the present invention may find applications as viscoelastics useful in surgery. Viscoelastic agents used in surgery may perform a number of different functions, including, without limitation, maintenance and support of soft tissue, tissue manipulation, lubrication, tissue protection, and adhesion prevention. As will be appreciated by one skilled in the art, the Theological properties of the polymers will necessarily affect their ability to perform these functions, and, as a result, their suitability for certain surgical procedures.

Viscoelastics are, for example, used in opththalmic surgery, such as cataract surgery. Cataracts, which are opacities of the natural ocular lens, can strike people in their 40s and 50s, but they occur most commonly in those over age 60—with a rapid increase in prevalence after that. More than 50% of all Americans 65 and older have cataracts, increasing to 70% among those over 75. In order to improve eyesight, the cataractous lens is surgically removed from the eye and an artificial intraocular lens is inserted in its place. Viscoelastics were introduced in the early 1980s in response to the observation that, during cataract surgery, the underside of the cornea was often damaged due to contact with instruments, devices, fluid bubbles, and intraocular lenses. Because the cells in this region cannot regrow, there was a need to protect them. Thus, during these surgical procedures, viscoelastic materials are typically injected into the anterior chamber of the eye to prevent collapse of the anterior chamber and to protect the delicate eye tissues from damage resulting from physical manipulation. Viscoelastics also gently inflate spaces inside the eye, making it easier to maneuver various tools inside the eye.

Other examples of ocular surgery procedures that employ viscoelastics include trabeculectomy (i.e., glaucoma filtration surgery), and vitrectomy (i.e., replacement of the vitrous, a normally clear, gel-like substance that fills the center of the eye), which may be performed to clear blood and debris from the eye, to remove scar tissue, or to alleviate traction on the retina.

Tissue Space Fillers

Polymers of the present invention may find applications as tissue space fillers in any of a wide variety of soft tissue augmentation procedures, including, but not limited to, reconstruction or cosmetic enhancement, treatment for stress urinary incontinence, and treatment of vocal cord problems (e.g., paralysis, atrophy or paresis).

Reconstruction or Cosmetic Enhancement Procedures. Tissue space fillers are used to correct deformities or to reconstruct areas that are missing or defective due to surgical intervention, trauma, disease, aging, or congenital condition. Examples of reconstruction or cosmetic enhancement procedures include, but are not limited to, dermal tissue augmentation; filling of lines, folds, wrinkles, minor facial depressions, cleft lips and the like, especially in the face and neck; correction of minor deformities due to aging or disease, including in the hands and feet, fingers and toes; dermal filling of sleep lines and expression lines; replacement of dermal and subcutaneous tissue lost due to aging; lip augmentation; filling of crow's feet and the orbital groove around the eye; breast augmentation; chin augmentation; augmentation of the cheek and/or nose; filling of indentations in the soft tissue, dermal or subcutaneous, due to, e.g., overzealous liposuction or other trauma; filling of acne or traumatic scars and rhytids; filling of nasolabial lines, nasoglabellar lines and infraoral lines.

Urinary Incontinence. Urinary incontinence is an underserved market: there are approximately 40 million people in the U.S. that suffer from urinary incontinence, yet there are only about 250,000 procedures performed each year. Collagen bulking agents are generally used to treat urinary incontinence. They are injected into tissue surrounding the urethra to tighten the urethral sphincter and stop urine from leaking. However, these agents require several injections across multiple appointments. They also have a poor cure rate of approximately 27% to 36%. If the procedure is successful, the success is only temporary as the collagen reabsorbs into the surrounding tissue. A carbon-bead based product (Durasphere™, Advanced UroScience, Inc., Saint Paul, Minn.)

entered the market in 1999 with the promise of permanence (due to less degradation of the material) but clinical data have not supported those claims and the product appears to have similar performance to collagen. Q-Med AB (Uppsala, Sweden) recently introduced Zuidex™, an HA gel which is reinforced by the addition of dextranomer, that promises immediate effects and ease of administration. New biomaterials, such as the inventive polysaccharide mimic polymers, could impact the market if they require less material, fewer injections and had better longevity.

Vocal Cord Augmentation. In vocal cord disorders such as paralysis, atrophy and paresis, one or both vocal cords are weakened and lack the ability to close and thus vibrate properly, resulting in a soft, breathy or weak voice. The affected cord may also allow food and liquids into the trachea or lungs causing difficulty with swallowing and coughing. Vocal cord paralysis may be caused by chest and neck surgery, brain injury, neck injury, lung or thyroid cancer, certain neurologic conditions, or a viral infection. In older people, vocal cord atrophy is a common problem affecting voice production. Standard treatments of vocal cord disorders include voice therapy and surgery. In surgery, doctors attempt to add bulk to the injured vocal cord by injecting a substance (e.g., fat or collagen) into the cord. This moves the injured cord closer to the non-injured cord, allowing for better contact and improved speech and swallowing. Other substances are being studied for vocal cord augmentation including silicone paste, Teflon paste, calcium hydroxylapatite, and hyaluronic acid.

Anti-Adhesives

Polymers of the present invention may be used as anti-adhesives. Anti-adhesives are devices that keep tissues from abnormally joining together following surgery. These abnormal unions, called adhesions, may form between an incision in the abdominal wall and the small bowel after abdominal surgery, leading to chronic pain or even bowel obstruction. Adhesions also occur following gynecological surgery, resulting in fibrous scarring that may involve the uterus, bladder, bowel or ovaries and fallopian tubes, and that can, in the worst case, lead to infertility. A wide variety of approaches, including use of steroids, non-steroidal anti-inflammatory drugs and minimally invasive surgical techniques, have been used in an attempt to prevent adhesions. However, biodegradable barriers appear to be the most promising tools available for keeping adjacent organs separate following surgery (P. B. Arnold et al., Fertil. Steril., 2000, 73: 157-161). Examples of such barriers include, but are not limited to, anti-adhesive membranes that may be laid on localized areas of the peritoneum, such as Interceed Absorbable Adhesion Barrier (Johnson & Johnson Patient Care Inc., New Brunswick, N.J.); Preclude Surgical Membrane (.L. Gore Co., Flagstaff, Ariz.) and Seprafilm Surgical Membrane (Genzyme, Cambridge, Mass.); and viscous gels, such as Hyskon (Pharmacia, Piscataway, N.J.); Sepracoat (Genzyme) and Intergel (Lifecore Biomedical, Inc., Chaska, Minn.).

Additional uses and applications of the inventive polymers will be immediately apparent to those skilled in the art.

B. Dosages and Administration

In a method of treatment of the present invention, an inventive polymer, or a pharmaceutical composition thereof, will generally be administered in such amounts and for such a time as is necessary or sufficient to achieve at least one desired result. As will be appreciated by one skilled in the art, the desired result may vary depending on the condition to be treated (e.g., osteoarthritis, cataract, dermal or subcutaneous tissue loss, urinary incontinence, or vocal cord disorder) and the purpose of the polymer (e.g., viscosupplementation, tissue augmentation, adhesion prevention, or soft tissue maintenance, support or protection). Thus, for example, in certain embodiments, a polymer of the present invention may be administered to the knee joint of a patient suffering from osteoarthritis in such amounts and for such a time that it provides pain relief, prevents or reduces swelling, prevents or reduces loss of motion of the joint and/or or improves motion of the joint. In other embodiments, a polymer of the present invention may be administered to the eye of a patient undergoing cataract surgery in such amounts that it allows maintenance and support of soft tissue, tissue manipulation, lubrication, tissue protection, or adhesion prevention. In yet other embodiments, a polymer of the present invention may be administered to the skin of a patient undergoing a cosmetic procedure in such amounts and for such a time that lines, folds, wrinkles or minor facial depressions are filled.

A treatment according to the present invention may consist of a single dose or a plurality of doses over a period of time. Administration may be one or multiple times daily, weekly (or at some other multiple day interval) or on an intermittent schedule. The exact amount of an inventive polymer, or a pharmaceutical composition thereof, to be administered will vary from subject to subject and will depend on several factors (see below).

Polymers of the present invention, or pharmaceutical compositions thereof, may be administered using any route of administration effective for achieving the desired effect. Administration will generally be local rather than systemic. Methods of local administration include, but are not limited to, dermal, intradermal, intramuscular, intraperitoneal, subcutaneous, ocular, and intra-articular routes.

Depending on the route of administration, effective doses may be calculated according to the body weight, body surface area, or organ size of the subject to be treated. Optimization of the appropriate dosages can readily be made by one skilled in the art in light of pharmacokinetic data observed in human clinical trials. Alternatively or additionally, the dosage to be administered can be determined from studies using animal models for the particular type of condition to be treated, and/or from animal or human data obtained from agents which are known to exhibit similar pharmacological activities. The final dosage regimen will be determined by the attending surgeon or physician, considering various factors which modify the action of active agent, e.g., the agent's specific activity, the agent's specific half-life in vivo, the severity of the condition and the responsiveness of the patient, the age, condition, body weight, sex and diet of the patient, the severity of any present infection, time of administration, the use (or not) of other concomitant therapies, and other clinical factors.

C. Combination Therapies

It will be appreciated that methods of treatment of the present invention can be employed in combination with additional therapies (i.e., a treatment according to the present invention can be administered concurrently with, prior to, or subsequently to one or more desired therapeutics or medical procedures). The particular combination of therapies (therapeutics or procedures) to employ in such a combination regimen will take into account compatibility of the desired therapeutics and/or procedures and the desired therapeutic effect to be achieved.

Thus, for example, in methods where a polysaccharide mimic polymer of the present invention is administered as a viscosupplement to a patient suffering from osteoarthritis, the patient may further receive a non-steroidal or steroidal anti-inflammatory drug and/or may undergo physical therapy. Alternatively or additionally, the inventive polymer may be administered in combination with another viscosupplement, e.g., hyaluronate, chitosan. Alternatively or additionally, the inventive polymer may be administered in combination with another aqueous soluble polymer, e.g., PEG, PEO, PAA.

In many methods of the present invention, a polysaccharide mimic polymer is administered as part of a surgical or clinical procedure. For example, a polymer used as a viscoelastic agent may be administered during cataract surgery. An inventive polymer used as a tissue space filler may be administered during surgery for the treatment of urinary incontinence, during a tissue augmentation procedure for treatment of vocal cord problems, or during a cosmetic procedure, e.g., for wrinkle filling. An inventive polymer used as an anti-adhesive agent may be administered during abdominal or gynecologic surgery to prevent formation of adhesions following surgery.

IV. Pharmaceutical Compositions of Polysaccharide Substitutes

As mentioned above, methods of treatment of the present invention include administration of an inventive polymer per se or in the form of a pharmaceutical composition. A pharmaceutical composition will generally comprise an effective amount of at least one inventive polymer and at least one pharmaceutically acceptable carrier or excipient.

Pharmaceutical compositions of the present invention may be formulated according to general pharmaceutical practice (see, for example, *"Remington's Pharmaceutical Sciences"* and *"Encyclopedia of Pharmaceutical Technology"*, J. Swarbrick, and J. C. Boylan (Eds.), Marcel Dekker, Inc: New York, 1988). The optimal pharmaceutical formulation can be varied depending upon the route of administration and desired dosage. Such formulations may influence the physical state, stability, rate of in vivo release, and rate of in vivo clearance of the administered compounds. Formulation will preferably produce liquid or semi-liquid (e.g., gel) pharmaceutical compositions.

Pharmaceutical compositions may be formulated in dosage unit form for ease of administration and uniformity of dosage. The expression "unit dosage form", as used herein, refers to a physically discrete unit of polysaccharide mimic polymer for the patient to be treated. Each unit contains a predetermined quantity of active material calculated to produce the desired effect. It will be understood, however, that the total dosage of the composition will be decided by the attending physician within the scope of sound medical judgment.

Formulation of pharmaceutical compositions of the present invention will mainly depend on the form of administration chosen. In certain embodiments, injectable formulations (e.g., solutions, dispersions, suspensions, emulsions) will be preferred, for example, for administration to a joint (e.g., knee), an intervertebral disc, the urinary system, or the vocal cord. Injectable formulations can also be used for certain reconstruction or cosmetic procedures. Other procedures may alternatively use gels, lotions, creams, ointments, plasters, bandages, sheets, foams, films, sponges, dressings, or bioadsorbable patches that can be applied to the area in need of treatment.

Formulation

Physiologically acceptable carriers, vehicles, and/or excipients for use with pharmaceutical compositions of the present invention can be routinely selected for a particular use by those skilled in the art. These include, but are not limited to, solvents, buffering agents, inert diluents or fillers, suspending agents, dispersing or wetting agents, preservatives, stabilizers, chelating agents, emulsifying agents, anti-foaming agents, ointment bases, penetration enhancers, humectants, emollients, and skin protecting agents.

Examples of solvents include water, Ringer's solution, U.S.P., isotonic sodium chloride solution, alcohols, vegetable, marine and mineral oils, polyethylene glycols, propylene glycols, glycerol, and liquid polyalkylsiloxanes. Inert diluents or fillers may be sucrose, sorbitol, sugar, mannitol, microcrystalline cellulose, starches, calcium carbonate, sodium chloride, lactose, calcium phosphate, calcium sulfate, or sodium phosphate. Examples of buffering agents include citric acid, acetic acid, lactic acid, hydrogenophosphoric acid, and diethylamine. Suitable suspending agents include, for example, naturally-occurring gums (e.g., acacia, arabic, xanthan, and tragacanth gum), celluloses (e.g., carboxymethyl-, hydroxyethyl-, hydroxypropyl-, and hydroxypropylmethylcellulose), alginates and chitosans. Examples of dispersing or wetting agents are naturally-occurring phosphatides (e.g., lecithin or soybean lecithin), condensation products of ethylene oxide with fatty acids or with long chain aliphatic alcohols (e.g., polyoxyethylene stearate, polyoxyethylene sorbitol monooleate, and polyoxyethylene sorbitan monooleate).

Preservatives may be added to a pharmaceutical composition of the present invention to prevent microbial contamination that can affect the stability of the formulation and cause infection in the patient. Suitable examples of preservatives include parabens (such as methyl-, ethyl-, propyl-, p-hydroxy-benzoate, butyl-, isobutyl- and isopropyl-paraben), potassium sorbate, sorbic acid, benzoic acid, methyl benzoate, phenoxyethanol, bronopol, bronidox, MDM hydantoin, iodopropylnyl butylcarbamate, benzalconium chloride, cetrimide, and benzylalcohol. Examples of chelating agents include sodium EDTA and citric acid.

Examples of emulsifying agents are naturally-occurring gums, naturally-occurring phosphatides (e.g., soybean lecithin, sorbitan mono-oleate derivatives), sorbitan esters, monoglycerides, fatty alcohols, and fatty acid esters (e.g., triglycerides of fatty acids). Anti-foaming agents usually facilitate manufacture, they dissipate foam by destabilizing the air-liquid interface and allow liquid to drain away from air pockets. Examples of anti-foaming agents include simethicone, dimethicone, ethanol, and ether.

Examples of gel bases or viscosity-increasing agents are liquid paraffin, polyethylene, fatty oils, colloidal silica or aluminum, glycerol, propylene glycol, carboxyvinyl polymers, magnesium-aluminum silicates, hydrophilic polymers (such as, for example, starch or cellulose derivatives), water-swellable hydrocolloids, carragenans, hyaluronates, and alginates. Ointment bases suitable for use in the pharmaceutical compositions of the present invention may be hydrophobic or hydrophilic; and specific examples include paraffin, lanolin, liquid polyalkylsiloxanes, cetanol, cetyl palmitate, vegetable oils, sorbitan esters of fatty acids, polyethylene glycols, and condensation products between sorbitan esters of fatty acids, ethylene oxide (e.g., polyoxyethylene sorbitan monooleate), and polysorbates.

Examples of humectants are ethanol, isopropanol glycerin, propylene glycol, sorbitol, lactic acid, and urea. Suitable emollients include cholesterol and glycerol. Examples of skin protectants include vitamin E, allatoin, glycerin, zinc oxide, vitamins, and sunscreen agents.

In certain embodiments, pharmaceutical compositions of the present invention may, alternatively or additionally, comprise other types of excipients including, thickening agents, bioadhesive polymers, and permeation enhancing agents.

Thickening agents are generally used to increase viscosity and improve bioadhesive properties of pharmaceutical compositions. Examples of thickening agents include, but are not limited to, celluloses, polyethylene glycol, polyethylene oxide, naturally occurring gums, gelatin, karaya, pectin, alginic acid, and povidone. In certain embodiments, a thickening agent is selected for its thioxotropic properties (i.e., has a viscosity that is decreased by shaking or stirring). The presence of such as an agent in a pharmaceutical composition allows the viscosity of the composition to be reduced at the time of administration to facilitate its application, e.g., to a skin area to be repaired, and to increase after application so that the composition remains at the site of administration.

Permeation enhancing agents are vehicles containing specific agents that affect the delivery of active components through the skin. Permeation enhancing agents are generally divided into two classes: solvents and surface active compounds (amphiphilic molecules). Examples of solvent permeation enhancing agents include alcohols (e.g., ethyl alcohol, isopropyl alcohol), dimethyl formamide, dimethyl sulfoxide, 1-dodecylazocyloheptan-2-one, N-decyl-methylsulfoxide, lactic acid, N,N-diethyl-m-toluamide, N-methylpyrrolidone, nonane, oleic acid, petrolatum, polyethylene glycol, propylene glycol, salicylic acid, urea, terpenes, and trichloroethanol. The surfactant permeation enhancing agent in the present inventive pharmaceutical compositions may be nonionic, amphoteric, cationic, anionic, or zwitterionic. Suitable nonioinic surfactants include poly(oxyethylene)-poly (oxypropylene) block copolymers, commercially known as poloxamers; ethoxylated hydrogenated castor oils; polysorbates, such as Tween 20 or Tween 80. Amphoteric surfactants include quaternized imidazole derivatives; cationic surfactants include cetypyridinium chloride, "soap" (fatty acid), alkylsulfonic acid salts (the main component of synthetic detergent, such as linear alkyl benzene sulfonate (LAS)), fatty alcohol sulfate (the main component of shampoo or old neutral detergents); and zwitterionic surfactants include the betaines and sulfobetaines.

Injectable formulations can be sterilized, for example, by filtration through a bacterial-retaining filter, by incorporating sterilizing agents in the form of sterile solid compositions which can be dissolved or dispersed in sterile water or other sterile injectable medium prior to use, or by irradiation sterilization (e.g., gamma and e-beam).

Bioactive Agents

In certain embodiments, the inventive polymer(s) is(are) the only active ingredient(s) in an inventive pharmaceutical composition. In other embodiments, the pharmaceutical composition further comprises one or more bioactive agents. As already mentioned above, a bioactive agent may be associated with the inventive polymer. Alternatively or additionally, a bioactive agent may be added to the composition of polymer and does not form any associations with the polymer.

As will be appreciated by one skilled in the art, selection of one or more bioactive agents as component(s) of an inventive pharmaceutical composition will be based on the intended purpose of the pharmaceutical composition (e.g., use in viscosupplementation in the treatment of joints, use as viscoelastics in cataract surgery, use as tissue space fillers for cosmetic procedures, treatment of urinary incontinence or treatment of vocal cord problems, or use as anti-adhesives for wound care).

In general, the amount of bioactive agent present in an inventive pharmaceutical composition will be the ordinary dosage required to obtain the desired result through local administration. Such dosages are either known or readily determined by the skilled practitioner in the pharmaceutical and/or medical arts.

Examples of bioactive agents that can be present in a pharmaceutical composition of the present invention include, but are not limited to, analgesics, anesthetics, pain-relieving agents, antimicrobial agents, antibacterial agents, antiviral agents, antifungal agents, antibiotics, anti-inflammatory agents, antioxidants, antiseptic agents, antipruritic agents, immunostimulating agents, and dermatological agents. Specific examples of suitable bioactive agents are provided and discussed below.

Pain Relieving Agents. A bioactive agent may be selected for its ability to prevent or alleviate pain, soreness or discomfort, to provide local numbness or anesthesia, and/or to prevent or reduce acute post-operative surgical pain. Thus, suitable pain relieving agents include, but are no limited to, compounds, molecules or drugs which, when applied locally, have a temporary analgesic, anesthetic, numbing, paralyzing, relaxing or calming effect.

Analgesics suitable for use in the present invention include non-steroidal, anti-inflammatory drugs (NSAIDs). NSAIDs have analgesic, antipyretic and anti-inflammatory activity. They act peripherally to provide their analgesic effect by interfering with the synthesis of prostaglandin, through cyclooxygenase (COX) inhibition. There are many different types of NSAIDs, including aspirin and other salicylates. Examples include, but are not limited to, ibuprofen, naproxen, sulindac, diclofenac, piroxicam, ketoprofen, diflunisal, nabumetone, etodolac, oxaprozin, and indomethacin. Aspirin is anti-inflammatory when administered in high doses, otherwise it is just a pain killer like acetaminophen. Acetaminophen has similar analgesic and antipyretic effects to the NSAIDs, but does not provide an anti-inflammatory effect. Several of the more potent NSAIDs have been developed into topical products for local administration to painful areas of the body.

Analgesics suitable for use in the present invention also include opioids. As used herein, the term "opioid" refers to any agonists or antagonists of opioid receptors such as the μ-, κ-, and δ-opioid receptors and different subtypes. Examples of opioids include, but are not limited to, alfentanil, allylprodine, alphaprodine, amiphenazole, anileridine, benzeneacetamine, benzoylhydrazone, benzylmorphine, benzitramide, nor-binaltorphimine, bremazocine, buprenorphine, butorphanol, clonitazene, codeine, cyclazocine, desomorphine, dextromoramide, dezocine, diampromide, dihydrocodeine, dihydrocodeine enol acetate, dihydromorphine, dimenoxadol, dimepheptanol, dimethyl-thiambutene, dioxaphetyl butyrate, dipipanone, diprenorphine, eptazocine, ethoheptazine, ethylketocyclazocine, ethylmethylthiambutene, etonitazene, etorphine, fentanyl, hydrocodone, hydromorphone, hydroxypethidine, isomethadone, ketobemidone, levallorphan, levorphanol, lofentanil, loperamide, meperidine, meptazinol, metazocaine, methadone, metopon, morphine, morphiceptin, myrophine, nalbuphine, nalmefene, nalorphine, naltrindole, naloxone, naltrexone, narceine, nicomorphine, norlevorphanol, normethadone, normorphine, norpipanone, opium, oxycodone, oxymorphone, papaveretum, papaverine, pentazocine, phenadoxone, phenazocine, phenoperidine, piminodine, piperidine, pirtramide, proheptazine, promedol, propiram, propoxyphene, remifentanil, spiradoline, sufentanil, tilidine, trifluadom, and active derivatives, prodrugs, analogs, pharmaceutically acceptable salts, or mixtures thereof.

Examples of peptide opioids include, but are not limited to, [Leu$^5$]enkephalin, [Met$^5$]enkephalin, Dynorphin A, Dynorphin B, α-Neoendorphin, β-Neoendorphin, $\beta_h$-Endorphin, Deltorphin II, Morphiceptin, and active derivatives, analogs, pharmaceutically acceptable salts, or mixtures thereof.

Tricyclic antidepressants can be useful as adjuvant analgesics. They are known to potentiate the analgesic effects of opioids (V. Ventafridda et al., Pain, 1990, 43: 155-162) and to have innate analgesic properties (M. B. Max et al., Neurology, 1987, 37: 589-596; B. M. Max et al., Neurology, 1988, 38: 1427-1432; R. Kishore-Kumar et al., Clin. Pharmacol. Ther., 1990, 47: 305-312). Tricyclic antidepressants include, but are not limited to, amitriptyline, amoxapine, clomipramine, desipramine, doxepin, imipramine, nortriptyline, protriptyline, and trimipramine.

Anesthetics that are suitable for use in the practice of the present invention include sodium-channel blockers. Examples of sodium-channel blockers include, but are not limited to, ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, etidocaine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocalne, procaine, propanocaine, proparacaine, propipocaine, propoxycaine, pseudococaine, pyrrocaine, ropivacaine, salicyl alcohol, tetracaine, tolycaine, trimecaine, zolamine, and active derivatives, prodrugs, analogs, pharmaceutically acceptable salts, or mixtures thereof.

Local anesthetics with different pharmacodynamics and pharmacokinetics may be combined in an inventive pharmaceutical composition in order to improve the effectiveness and tolerance of the composition. For example, an inventive composition may comprise an euctectic mixture of lidocaine and prilocalne, or a mixture of lidocaine and tetracaine. It has been reported (see, for example, U.S. Pat. Nos. 5,922,340 and 6,046,187) that co-administration of a glucocorticosteroid and a local anesthetic may prolong or otherwise enhance the effect of local anesthetics. Examples of glucocorticosteroids include dexamethazone, cortisone, hydrocortisone, prednisone, predriisolone, beclomethasone, betamethasone, flunisolide, fluocinolone, acetonide, fluocinonide, triamcinolone, and the like.

Locally acting vasoconstructive agents are also known to provide effective enhancement of local anesthesia, especially when administered through controlled release. Examples of vasoconstrictor agents include, but are not limited to, catechol amines (e.g., epinephrine, norepinephrine and dopamine); metaraminol, phenylephrine, sumatriptan and analogs, alpha-1 and alpha-2 adrenergic agonists, such as, for example, clonidine, guanfacine, guanabenz, and dopa (i.e., dihydroxyphenylalanine), methyldopa, ephedrine, amphetamine, methamphetamine, methylphenidate, ethylnorepinephrine ritalin, pemoline, and other sympathomimetic agents.

Anti-Infective Agents. Anti-infective agents for use in pharmaceutical compositions of the present invention are compounds, molecules or drugs which, when administered locally, have an anti-infective activity (i.e., they can decrease the risk of infection; prevent infection; or inhibit, suppress, combat or otherwise treat infection). Anti-infective agents include, but are not limited to, antiseptics, antimicrobial agents, antibiotics, antibacterial agents, antiviral agents, antifungal agents, anti-protozoan agents, and immunostimulating gents.

Antiviral agents suitable for use in the present invention include RNA synthesis inhibitors, protein synthesis inhibitors, immunostimulating agents, and protease inhibitors. Antiviral agents may, for example, be selected from the group consisting of acyclovir, amantadine hydrochloride, foscarnet sodium, ganeiclovir sodium, phenol, ribavirin, vidarabine, and zidovudine.

Examples of suitable antifungal agents include lactic acid, sorbic acid, Amphotericin B, Ciclopirox, Clotrimazole, Enilconazole, Econazole, Fluconazole, Griseofulvin, Halogropin, Introconazole, Ketoconazole, Miconazole, Naftifine, Nystatin, Oxiconazole, Sulconazole, Thiabendazole, Terbinafine, Tolnaftate, Undecylenic acid, Mafenide, Silver Sulfadiazine, and Carbol-Fushsin.

Antibiotics and other antimicrobial agents may be selected from the group consisting of bacitracin; the cephalosporins (such as cefadroxil, cefazolin, cephalexin, cephalothin, cephapirin, cephradine, cefaclor, cefamandole, cefonicid, ceforanide, cefoxitin, cefuroxime, cefoperazone, cefotaxime, cefotetan, ceftazidime, ceftizoxime, ceftriaxone, and meropenem); cycloserine; fosfomycin, the penicillins (such as amdinocillin, ampicillin, amoxicillin, azlocillin, bacamipicillin, benzathine penicillin G, carbenicillin, cloxacillin, cyclacillin, dicloxacillin, methicillin, mezlocillin, nafcillin, oxacillin, penicillin G, penicillin V, piperacillin, and ticarcillin); ristocetin; vancomycin; colistin; novobiocin; the polymyxins (such as colistin, colistimathate, and polymyxin B); the aminoglycosides (such as amikacin, gentamicin, kanamycin, neomycin, netilmicin, paromomycin, spectinomycin, streptomycin, and tobramycin), the tetracyclines (such as demeclocycline, doxycycline, methacycline, minocycline, and oxytetracycline); carbapenems (such as imipenem); monobactams (such as aztreonam); chloramphenicol; clindamycin; cycloheximide; fucidin; lincomycin; puromycin; rifampicin; other streptomycins; the macrolides (such as erythromycin and oleandomycin); the fluoroquinolones; actinomycin; ethambutol; 5-fluorocytosine; griseofulvin; rifamycins; the sulfonamides (such as sulfacytine, sulfadiazine, sulfisoxazole, sulfamethoxazole, sulfamethizole, and sulfapyridine); and trimethoprim.

Other antibacterial agents include, but are not limited to, bismuth containing compounds (such as bismuth aluminate, bismuth subcitrate, bismuth subgalate, and bismuth subsalicylate); nitrofurans (such as nitrofurazone, nitrofurantoin, and furozolidone); metronidazole; tinidazole; nimorazole; and benzoic acid.

Antiseptic agents may be selected from the group consisting of benzalkonium chloride, chlorhexidine, benzoyl peroxide, hydrogen peroxide, hexachlorophene, phenol, resorcinol, and cetylpyridinium chloride.

The risk of infection is directly influenced by a suppressed immune system due to disease or medication. Immunostimulating agents are compounds, molecules or drugs that stimulate the immune system of a patient to respond to the presence of a foreign body, for example, by sending macrophages to the infected site(s). Immunostimulating agents suitable for use in the present invention may be selected from a wide range of therapeutic agents, such as interleukin 1 agonists, interleukin 2 agonists, interferon agonists, RNA synthesis inhibitors, and T cell stimulating agents.

Anti-Inflammatory Agents. Anti-inflammatory agents for use in pharmaceutical compositions of the present invention are compounds, molecules or drugs which, when administered locally, have an anti-inflammatory activity (i.e., they can prevent or reduce the duration and/or severity of inflammation; prevent or reduce injury to cells at the injured/damaged site; prevent or reduce damage or deterioration of surrounding tissue due to inflammation; and/or provide relief from at least one of the manifestations of inflammation such as erythema, swelling, tissue ischemia, itching, fever, scarring, and the like).

Anti-inflammatory agents include NSAIDs and steroidal anti-inflammatory agents. Examples of NSAIDs can be found above. Examples of steroidal anti-inflammatory agents include, but are not limited to, aclomethasone dipropionate, flunisolide, fluticasone, budesonide, triamcinolone, triamcinoline acetonide, beclomethasone diproprionate, betamethasone valerate, betamethasone diproprionate, hydrocortisone, cortisone, dexamethason, mometasone furoate, prednisone, methylprednisolone aceponate, and prednisolone.

Anti-inflammatory agents may, alternatively or additionally, be selected from the wide variety of compounds, molecules, and drugs exhibiting antioxidant activity. Antioxidants are agents that can prevent or reduce oxidative damage to tissue. Examples of antioxidants may include, but are not limited to, vitamin A (retinal), vitamin B (3,4-didehydroretinol), vitamin C (D-ascorbic acid, L-ascorbic acid), α-carotene, β-carotene, γ-carotene, δ-carotene, vitamin E (α-tocopherol), β-tocopherol, γ-tocopherol, δ-tocopherol, tocoquinone, tocotrienol, butylated hydroxy anisole, cysteine, and active derivatives, analogs, precursors, prodrugs, pharmaceutically acceptable salts or mixtures thereof.

Other Bioactive Agents

In certain embodiments, the bioactive agent is a biomolecule that is naturally present in the body and/or that is naturally secreted at an injured or damaged site (i.e., body area) and plays a role in the natural healing process. As will be apparent to those of ordinary skill in the art, variants, synthetic analogs, derivatives, and active portions of these biomolecules can, alternatively, be used in the inventive compositions as long as they exhibit substantially the same type of property/activity as the native biomolecule. Such variants, synthetic analogs, derivatives or active portions are intended to be within the scope of the term "bioactive agents".

Bioactive biomolecules may be extracted from mammalian tissues and used in inventive pharmaceutical compositions either crude or after purification. Alternatively, they may be prepared chemically or by conventional genetic engineering techniques, such as via expression of synthetic genes or of genes altered by site-specific mutagenesis.

Examples of suitable bioactive biomolecules include cytokines and growth factors. Cytokines and growth factors are polypeptide molecules that regulate migration, proliferation, differentiation and metabolism of mammalian cells. A diverse range of these biomolecules have been identified as potentially playing an important role in regulating healing. Examples of cytokines include, but are not limited to, interleukins (ILs) (e.g., IL-1, IL-2, IL-4 and IL-8), interferons (IFNs) (e.g., IFN-α, IFN-β, and IFN-γ), and tumor necrosis factors (e.g., TNF-α), or any variants, synthetic analogs, active portions or combinations thereof. Examples of growth factors include, but are not limited to, epidermal growth factors (EGFs), platelet-derived growth factors (PDGFs), heparin binding growth factor (HBGFs), fibroblast growth factors (FGFs), vascular endothelial growth factors (VEGFs), insulin-like growth factors (IGFs), connective tissue activating peptides (CTAPs), transforming growth factors alpha (TGF-α) and beta (TGF-β), nerve growth factor NGFs), colony stimulating factors (G-CSF and GM-CSF), and the like, or any variants, synthetic analogs, active portions or combinations thereof.

Other examples of suitable bioactive biomolecules include proteoglycans, or portions thereof. Proteoglycans are protein-carbohydrate complexes characterized by their glycosaminoglycan (GAG) component. GAGs are highly charged sulfated and carboxylated polyanionic polysaccharides. Examples of GAGs suitable for use in pharmaceutical compositions of the present invention include, but are not limited to, hyaluronan, chondroitin sulfate, dermatan sulfate, heparan sulfate, and keratan sulfate.

Still other examples of suitable bioactive biomolecules include adhesion molecules. Adhesion molecules constitute a diverse family of extracellular and cell surface glycoproteins involved in cell-cell and cell-extracellular matrix adhesion, recognition, activation, and migration. Adhesion molecules are essential to the structural integrity and homeostatic functioning of most tissues, and are involved in a wide range of biological processes, including embryogenesis, inflammation, thrombogenesis, and tissue repair. Adhesion molecules include matricellular proteins (e.g., thrombospondins and tenascins), and cell surface adhesion molecules (e.g., integrins, selectins, cadherins, and immunoglobulins).

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Example 1

Synthesis of Polysaccharide Mimics

Experimental Section: All reactions were carried out at room temperature in oven-dried glassware. All solvents were distilled prior to use. Gel permeation chromatography (GPC) was performed either with tetrahydrofuran (THF) as eluent through a Water HR-5 organic column or with water as eluent through a Shodex-OH pack column. All molecular weights were measured against polystyrene standards for THF polymers and against dextran standards for water soluble polymers. Proton NMR spectra were recorded on a Varian Inova 4000 MHz spectrometer, chemical shifts are reported downfield from tetramethylsilane in parts per million. Broad or overlapping peaks, often observed in the spectra of polymers are denoted "br" below.

Ethyl-5-norbornene-2-carboxylate, 1

The monomer was prepared by combining oxalyl chloride (23.0 mL, 264 mmol), freshly distilled dichloromethane ($CH_2Cl_2$, 120 mL), and an endo/exo mixture of 5-norbornene-2-carboxylic acid (11.3 g, 0.0817 mol). One drop of dimethylformamide (DMF) was added that caused vigorous bubbling of the solution. After 40 minutes of stirring, the solvents were removed under vacuum to give an orange oil. This oil was dissolved in $CH_2Cl_2$ (100 mL), triethylamine (12.0 mL, 86.1 mmol), dimethylaminipyridine (1.00 g, 0.00818 mol) and ethanol (50 mL, 861.73 mmol). The solution was stirred for an additional 20 hours under nitrogen.

The solvents were then removed under vacuum at room temperature, which yielded a brown liquid. Vacuum distillation of the brown liquid yielded ethyl-5-norbornene-2-carboxylate, compound 1, as a 4:1 mixture of endo/exo isomers (9.62 g, 71% yield). $^1$H NMR ($CDCl_3$) δ 6.1 (dd, J=5.7 Hz, 3 Hz, endo H-6), 6.0-6.05 (m, exo H-5, H-6), 5.85 (dd, J=5.7 Hz, 3 Hz, endo H-5), 4.0 (m, 2H, H-9), 3.1 (s, endo H-4), 2.95 (s, exo H-4), 2.8-2.9 (m, 2H, H-1, H-2), 1.8-1.9 (m, 1H, H-3), 1.1 (t, J=7 Hz, 3H, H-10). $^{13}$C NMR ($CDCl_3$): δ174 (C-8), 137.5 (C-5), 132.2 (C-4), 59.9 (C-9), 49.5 (C-7), 45.4 (C-3), 43.1 (C-2), 42.4 (C-6), 29.1 (C-1), 14.1 (C-10). EI m/z 167 ($MH^+$).

Poly(ethyl-5-norbornene-2-carboxylate), 2

Polymer 2 was synthesized by first dissolving compound 1 (0.570 g, 3.43 mmol) in 19 mL of 8:1 (v:v) benzene:dichloromethane. Grubbs' catalyst (7 mg, 0.009 mmol) was added and the solution was stirred under nitrogen for 4 hours. An excess of ethyl vinyl ether was then added to terminate polymerization, and the solution was stirred for an additional 30 minutes. The solution was poured in 200 mL of methanol and the polymer precipitated.

Subsequent washes and drying yielded 0.510 g (90% yield) of poly(ethyl-5-norbornene-2-carboxylate), 2. $^1$H NMR (400 MHz, $CDCl_3$): δ 5.4-5.2 (br m, H-5, 6), 4.0 (br m, H-8), 3.0-2.4 (br m, H-1,2,4), 2.0-1.4 (br m, H-3,7), 1.1 (br m, H-9). $M_w$=187,600, $M_n$=172,100, PDI=1.09.

The molecular weight of polymer 2 can be modulated from 1,000 to 10,000,000 using different ratio of Grubbs' catalyst (see FIG. 3).

Poly(ethyl-5,6-dihydroxynorbornane-2-carboxylate), 3

The dihydroxylated polymer, 3, was prepared by dissolving poly(ethyl-5-norbornene-2-carboxylate), 2, (1.25 g, 7.68 mole of repeating units) and tetraethylammonium trifluoroacetate (TEA-TFA, 3.5 mM) in $CH_2Cl_2$ (12.6 mL) and cooled to 5° C. on ice. In another iced flask, 50% hydrogen peroxide ($H_2O_2$; 2.42 mL) was added to $CH_2Cl_2$ (9.4 mL). To this solution, trifluoroacetic anhydride (6.8 mL) was added dropwise.

Contents of the two flasks were combined and the resulting solution was refluxed at 45° C. for 4 hours. The solvents were removed under reduced pressure. Water was added to the residual oil to precipitate a white polymer, 3 (1.0 g, 80% yield). $^1$H NMR (400 MHz, $CDCl_3$) δ 5.4-3.8 (br m, H-5,6), 3.8-3.6 (br m, H-5, 6), 3.3-3.0 (m, H-7), 2.9-1.3 (br m, H-1, 2,3,4), 1.2 (m, H-8). $M_w$=158,700. $M_n$=146,000. PDI=1.09.

The molecular weight of polymer 3 can be modulated from 1,000 to 10,000,000 using different ratio of Grubbs' catalyst in the preparation of 2 (see FIG. 3).

Poly(5,6-dihydroxynorbornane-2-carboxylic acid), 4

The hydrophilic polymer 4 was synthesized by dissolving poly(ethyl-5,6-dihydroxynorbornane-2-carboxylate), 3 (1.0 g, 5.00 moles of repeating units and K2CO3 (0.30 g, 12.5 mmol) in $CH_3OH$ (28 mM) at 60° C. The solution was stirred for 4 hours at which point the methanol was removed under reduced pressure. One molar HCl was added to precipitate the polymer, 4 (0.523 g, 52% yield). $^1$H NMR ($D_2O$): δ 4.4-4.6 (br m, H-5,6), 3.1-3.4 (br m, H-5,6), 1-2.8 br m, H-1, 2, 3, 4, 7).

The molecular weight of polymer 4 can be modulated from 1,000 to 10,000,000 using different ratio of Grubbs' catalyst in the preparation of 2 (see FIG. 3).

Methyl-5-oxanorbornene-2-carboxylate, 5

In order to prepare monomer 5, the oxo-analog of 1, furan (1 mL, 0.137 mmol), methyl acrylate (0.9 mL, 0.0100 mmol) and the catalyst zinc iodide (962 mg, 0.003 mmol) were stirred at 40° C. for 68 hours. The solution was then diluted with 100 mM ethyl acetate and washed with 20 mM 0.1 M $Na_2SO_3$. After drying with $Na_2SO_4$ and filtration, the solvents were removed under reduced pressure to yield an orange liquid. Vacuum distillation of the orange liquid yielded methyl-5-oxanorbornene-2-carboxylate, compound 5, as a colorless liquid. $^1$H NMR (400 MHz, $CDCl_3$) δ 6.37 (m, 2H), 5.00 (s, 1H), 4.70 (d, J=4 Hz, 1H), 3.55 (s, 3H), 2.25 (m, 1H), 1.95 (m, 1H), 1.35 (m, 1H). Shifts are consistent with the exo product. EI m/z=155 ($MH^+$).

Poly(methyl-5-oxanorbornane-2-carboxylate), 6

Polymer 6 was synthesized by first dissolving methyl-5-oxanorbornane-2-carboxylate, 5, (1 g, 10.9 mmol) in 12.0 mL of 8:1 (v/v) benzene:dichloromethane. Grubbs' catalyst (0.14 mg, 0.14 μmol) was added and the solution was stirred under nitrogen for 4 hours. Ethyl vinyl ether was added to the solution and the solution was stirred for an additional 30 minutes to terminate the polymerization reaction. The solution was poured into 600 mL of methanol and the polymer precipitated.

Subsequent methanol washes and drying yielded 0.916 g (92% yield) of poly(methyl-5-oxanorbornane-2-carboxylate), 6, a white polymer. $^1$H NMR (400 MHz, DMSO) δ 5.7-5.2 (br m, H-5,6), 4.8-4.3 (br m, H-7), 3.60 (br m, $CH_3$), 3.2-1.7 (br m, H-1,2,3,4). $M_w$=3,400,000 PDI=1.2.

The molecular weight of polymer 6 can be modulated from 1,000 to 3,500,000 using different ratio of Grubbs' catalyst (see FIG. 3).

Poly(methyl-5,6-dihydroxyoxanorbornane-2-carboxylate), 7

Polymer 7 was prepared by combining poly(ethyl-5-norbornene-2-carboxylate), 6 (0.5114 g) and TEA-TFA (1.4 mL), followed by dissolution in $CH_2Cl_2$ (10.0 mL) and cooling to 5° C. on ice. In another iced flask, 50% $H_2O_2$ (0.96 mL) was added to $CH_2Cl_2$ (4.0 mL). To this solution trifluoroacetic anhydride (2.71 mL) was added drop-wise.

Contents of the two flasks were mixed and the resulting solution was refluxed at 45° C. for 4 hours. The solvents were then removed under reduced pressure. Water was added to the residual oil to precipitate a white polymer, 7 (0.477 g, 93% yield). $^1$H NMR (400 MHz, DMSO) δ 3.6 (br m, $CH_3$), 4.8-3.0 (br m, $CH_2$), 2.5-1.8 (br m, H-1, 2, 3, 4, 5, 6). $M_w$=3,000,000. PDI=1.5.

The molecular weight of polymer 7 can be modulated from 1,000 to 3,500,000 using different ratio of Grubbs' catalyst in the preparation of polymer 6 (see FIG. 3).

Poly(5,6-dihydroxyoxanorbornane-2-carboxylic acid), 8

The hydrophilic polymer 8 was synthesized as follows: Polymer 7 (0.2159 g) and $K_2CO_3$ (0.100 g, 0.725 mmole) were dissolved in $CH_3OH$ (15.0 mL) at 60° C. The solution was stirred for 4 hours at which point the methanol was removed under reduced pressure. The resulting pale orange residue was then dissolved in 1M HCl to yield the white, fibrous polymer, 8 (0.1111 mg, 52% yield). $^1$H NMR (DMSO): δ 4.8-3.0 (br m, $CH_2$), 2.5-1.8 (br m, H-1, 2, 3, 4, 5, 6).

The molecular weight of polymer 8 can be modulated from 1,000 to 3,500,000 using different ratio of Grubbs' catalyst in the preparation of polymer 6 (see FIG. 3).

Poly(5-oxanorbornane-2-sodium carboxylate salt), 9

Polymer 9 was prepared by combining poly(methyl-5-oxaborbomane-2-carboxylate), 6 (0.5 g) dissolved in THF (100 mL) and NaOH 1 M (50 mL). The solution was then stirred under nitrogen for 24 hours. After evaporation of the organic solvent, the polymer was precipitated by adding HCl 1 M.

Subsequent methanol washes and drying yielded 0.45 g (90% yield) of polymer 9, a white polymer. $^1$H NMR (400 MHz, DMSO) δ 5.7-5.2 (br m, H-5,6), 4.8-4.3 (br m, H-7), 3.2-1.7 (br m, H-1,2,3,4). $M_w$=3,400,000 PDI=1.3.

The molecular weight of polymer 9 can be modulated from 1,000 to 3,500,000 using different ratio of Grubbs' catalyst in the preparation of polymer 6 (see FIG. 3).

Poly(5-norbornene-2-sodium carboxylate salt), 10

Polymer 10 was prepared by combining poly(ethyl-5-norbornene-2-carboxylate), 2 (0.5 g) dissolved in THF (100 mL) and NaOH 1 M (50 mL). The solution was then stirred under nitrogen for 24 hours. After evaporation of the organic solvent, the polymer was precipitated by adding HCl 1 M.

Subsequent methanol washes and drying yielded 0.46 g (92% yield) of polymer 10, a white polymer. $^1$H NMR (400 MHz, DMSO) δ 5.4-5.2 (br m, H-5, 6), 3.0-2.4 (br m, H-1,2, 4), 2.0-1.4 (br m, H-3, 7), 1.1 (br m, H-9). $M_w$=500 PDI=1.3.

The molecular weight of polymer 10 can be modulated from 1,000 to 500,000 using different ratio of Grubbs' catalyst in the preparation of polymer 2 (see FIG. 3).

Example 2

Physical Properties of Polysaccharide Mimics

Figure 7:
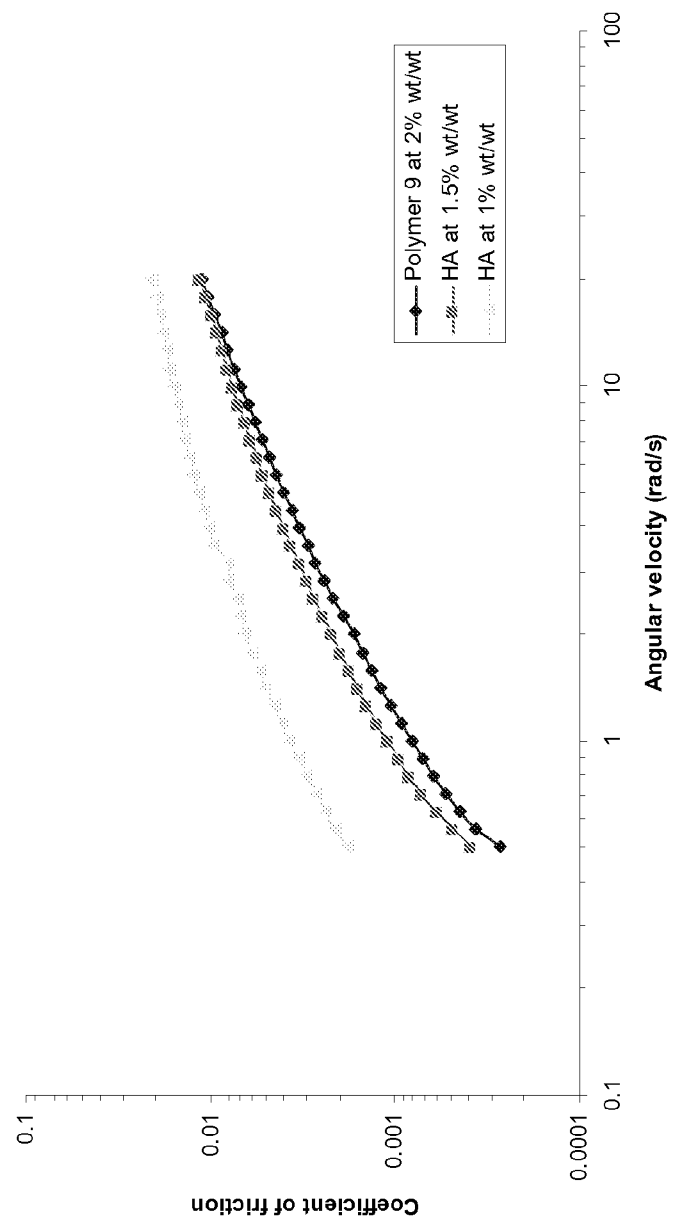
FIG. 7 presents coefficient of friction data for hyaluronic acid and polymer 9.

Coefficient of friction measurements were performed on a RA 1000 controlled strain rheometer from TA Instrument equipped with a peltier temperature control. A 40 mm diameter steel plate was used for the measurement of coefficients of friction. Coefficient of friction measurements were performed at 25° C. A normal force of 5N was applied to the viscoelastic material and an oscillatory frequency sweep (from 0.01 to 10 Hz) with a controlled strain of 1% was performed at 25° C. This measures the oscillation stress of the material, which can then be converted to coefficient of friction using the normal stress. Data are reported at a frequency of 1 Hz. As shown in FIG. 7, polymer 9 was found to have a coefficient of friction similar to HA.

Viscosity measurements were performed on a RA 1000 controlled strain rheometer from TA Instrument equipped with a peltier temperature control. A 40 mm diameter steel plate with a 2° angle with a gap of 47 μm was used for the measurement of the viscosity properties. Viscosity measurement was performed at 25° C. An oscillatory frequency sweep (from 0.01 to 10 Hz) with a controlled strain for a linear response was performed at 25° C. This measures the viscosity of the material. Data are reported at a frequency of 1 Hz.

Contact angles were calculated using a Ram-hart goniometer coupled to a CCD camera for imaging.

Contact angles measured for polymers of the present invention are listed in FIG. 3. Viscosity data obtained for polymers of the invention are presented on FIGS. 4 and 6, and coefficients of friction are presented on FIG. 7.

Example 3

Injection of Polysaccharide Mimics

Figure 8:
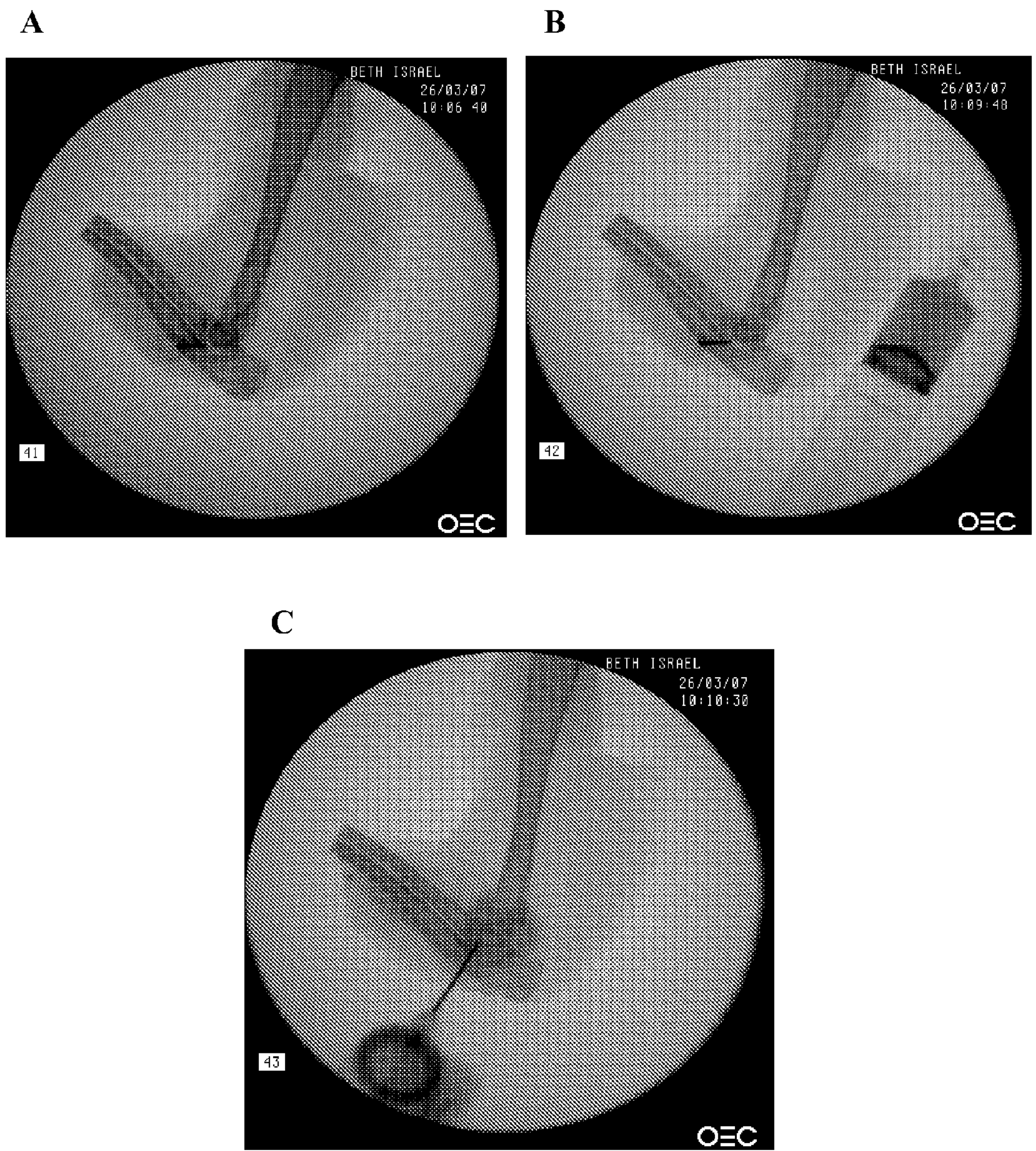
FIG. 8 is a set of X-ray pictures showing (A) a New Zealand White Rabbit elbow joint where the synovial joint space is being accessed using a 22 G needle; (B) the syringe used containing a mixture of contrast agent and polymer 9; and (C) a New Zealand White Rabbit elbow joint where the synovial joint space is filled with the mixture of polymer 9 and contrast agent.

New Zealand White Rabbit elbow joints were used to perform lubricant injections. Polymer 9 was mixed with an iodinated contrast agent (10% by volume) and stirred to ascertain a uniform mixture. The synovial joint space was accessed using a 22 G needle under fluoroscopic guidance (OEC 6600). The native synovial fluid was removed, then the mixture (containing the polymer and contrast agent) was injected into the joint space. The delivery of the mixture into the joint space was ascertained by X-ray. FIG. 8 shows X-ray pictures of a New Zealand White Rabbit elbow joint injected with the mixture of polymer 9 and contrast agent.

Other Embodiments

Other embodiments of the invention will be apparent to those skilled in the art from a consideration of the specification or practice of the invention disclosed herein. It is intended that the specification and Examples be considered as exemplary only, with the true scope of the invention being indicated by the following claims.

TABLE 1

| Polymer | $M_w$ | Monomer/Catalyst ratio | PDI | Contact Angle |
|---|---|---|---|---|
| 2 | 187,600 | 1,100 | 1.09 | 57-65 |
| | 350,000 | 2,100 | 1.1 | |
| | 500,000 | 3,000 | 1.1 | |
| | 10,000,000 | 60,000 | 1.2 | |
| 3 | 158,700 | | 1.09 | 30-40 |
| | 350,000 | | 1.1 | |
| | 500,000 | | 1.1 | |
| | 10,000,000 | | 1.2 | |
| 4 | 158,700 | | 1.2 | 9-12 |
| | 350,000 | | 1.1 | |
| | 500,000 | | 1.1 | |
| | 10,000,000 | | 1.2 | |
| 6 | 58,200 | 380 | 1.1 | 46-56 |
| | 350,000 | 2300 | 1.2 | |
| | 500,000 | 3200 | 1.3 | |
| | 3,500,000 | 22700 | 1.5 | |
| 7 | 50,200 | | 1.1 | 20-25 |
| | 340,000 | | 1.2 | |
| | 500,000 | | 1.3 | |
| | 3,500,000 | | 1.5 | |
| 8 | 52,200 | | 1.1 | 12-15 |
| | 350,000 | | 1.2 | |
| | 500,000 | | 1.2 | |
| | 3,500,000 | | 1.6 | |
| 9 | 52,200 | | 1.1 | 10-15 |
| | 350,000 | | 1.2 | |
| | 500,000 | | 1.2 | |
| | 3,400,000 | | 1.6 | |
| 10 | 158,700 | | 1.2 | 30-40 |
| | 350,000 | | 1.2 | |
| | 500,000 | | 1.3 | |

What is claimed is:

1. A polymer selected from the group consisting of:

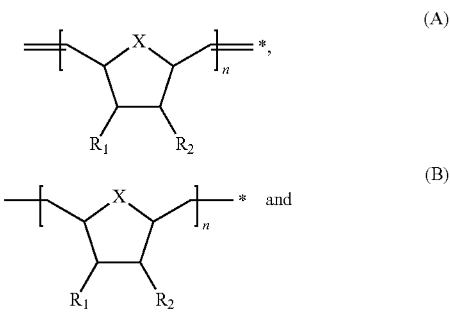

-continued (C)

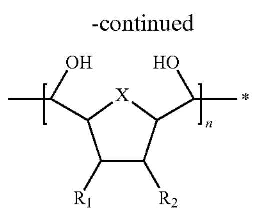

wherein:

n is an integer from 100 to 200,000; X is O; $R_1$ is H; $R_2$ is selected from the group consisting of COOR', CONHR', and SR', each occurrence of R' is independently selected from the group consisting of H, $Na^+$, an alkenyl, an alkynyl, $COCH_3$, $CH_2CH_2OH$, $CH_2CH_2OR''$, an amino acid, a small or large peptide, $COCCH_3{=}CH_2$, $COCH{=}CH_2$, $CH_2CO_2H$, $CH_2CH_2CO_2H$, $CH_2CH_2SH$, $CH_2CH_2SR''$ and $(CH_2CH_2O)_{n'}R'''$, n' is an integer from 1 to 2000; each occurrence of R" is independently selected from the group consisting of trityl, 4-methyltrityl and 2-pyridyl; and each occurrence of R''' is independently selected from the group consisting of H, an alkyl, an alkenyl, an alkynyl, $COCCH_3{=}CH_2$, $COCH{=}CH_2$, $CH_2CHO$, $CH_2CH_2CHO$, $CO_2H$, $CO_2R''''$, $CH_2CO_2H$, $CH_2CH_2CO_2H$, $CH_2NH_2$, $CH_2NHR''''$, $CH_2N(R'''')_2$, $CH_2CH_2NH_2$, $CH_2CH_2NHR$, $CH_2CH_2N(R'''')_2$, SH, $CH_2CO_2R''''$, and $CH_2CH_2CO_2R''''$, and each occurrence of R'''' is independently selected from the group consisting of maleimide, an amino acid, a small or large peptide, phosphate, sulfate, choline, and an activated ester.

2. The polymer of claim 1, wherein the polymer is a viscous liquid.

3. The polymer of claim 1, wherein the polymer is a gel.

4. A pharmaceutical composition comprising an effective amount of at least one pharmaceutically acceptable carrier and at least one polymer selected from the group consisting of:

(A)

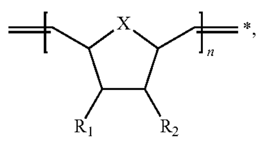

(B)

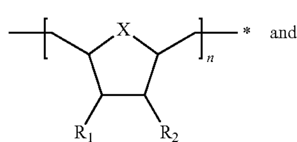

and (C)

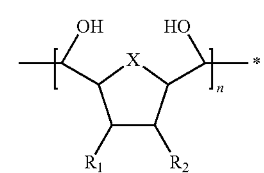

wherein:

n is an integer from 100 to 200,000; X is O; $R_1$ is H; $R_2$ is selected from the group consisting of COOR', CONHR', and SR', each occurrence of R' is independently selected from the group consisting of H, $Na^+$, an alkenyl, an alkynyl, $COCH_3$, $CH_2CH_2OH$, $CH_2CH_2OR''$, an amino acid, a small or large peptide, $COCCH_3{=}CH_2$, $COCH{=}CH_2$, $CH_2CO_2H$, $CH_2CH_2CO_2H$, $CH_2CH_2SH$, $CH_2CH_2SR''$ and $(CH_2CH_2O)_{n'}R'''$, n' is an integer from 1 to 2000; each occurrence of R" is independently selected from the group consisting of trityl, 4-methyltrityl and 2-pyridyl; and each occurrence of R''' is independently selected from the group consisting of H, an alkyl, an alkenyl, an alkynyl, $COCCH_3{=}CH_2$, $COCH{=}CH_2$, $CH_2CHO$, $CH_2CH_2CHO$, $CO_2H$, $CO_2R''''$, $CH_2CO_2H$, $CH_2CH_2CO_2H$, $CH_2NH_2$, $CH_2NHR''''$, $CH_2N(R'''')_2$, $CH_2CH_2NH_2$, $CH_2CH_2NHR$, $CH_2CH_2N(R'''')_2$, SH, $CH_2CO_2R''''$, and $CH_2CH_2CO_2R''''$, and each occurrence of R'''' is independently selected from the group consisting of maleimide, an amino acid, a small or large peptide, phosphate, sulfate, choline, and an activated ester.

5. The pharmaceutical composition of claim 4 further comprising a bioactive agent.

6. The pharmaceutical composition of claim 5, wherein the bioactive agent is a member of the group consisting of a growth factor, a cytokine, a small molecule, an analgesic, an anesthetic, an antimicrobial agent, an antibacterial agent, an antiviral agent, an antifungal agent, an antibiotic, an anti-inflammatory agent, an antioxidant, an antiseptic agent, and any combination thereof.

7. The pharmaceutical composition of claim 5, wherein the bioactive agent is a member of the group consisting of collagen, fat, silicone paste, TEFLON paste, calcium hydroxyapatite, hyaluronic acid, hyaluronates, and any combination thereof.

8. A method comprising the step of: administering an effective amount of a polymer to a subject in need thereof wherein the polymer is selected from the group consisting of:

(A)

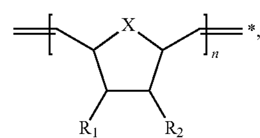

(B)

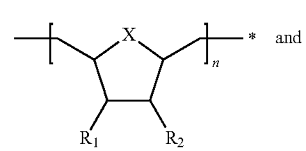

and (C)

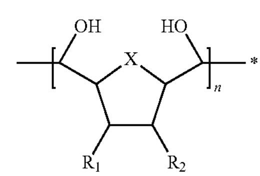

wherein:

n is an integer from 100 to 200,000; X is O; $R_1$ is H; $R_2$ is selected from the group consisting of COOR', CONHR', and SR', each occurrence of R' is independently selected from the group consisting of H, $Na^+$, an alkenyl, an alkynyl, $COCH_3$, $CH_2CH_2OH$, $CH_2CH_2OR''$, an amino acid, a small or large peptide, $COCCH_3{=}CH_2$, $COCH{=}CH_2$, $CH_2CO_2H$, $CH_2CH_2CO_2H$, $CH_2CH_2SH$, $CH_2CH_2SR''$ and $(CH_2CH_2O)_{n'}R'''$, n' is an integer from 1 to 2000; each occurrence of R" is independently selected from the group consisting of trityl, 4-methyltrityl and 2-pyridyl; and each occurrence of R''' is independently selected from the group consisting of H, an alkyl, an alkenyl, an alkynyl, $COCCH_3{=}CH_2$, $COCH{=}CH_2$, $CH_2CHO$, $CH_2CH_2CHO$, $CO_2H$, $CO_2R''''$, $CH_2CO_2H$, $CH_2CH_2CO_2H$, $CH_2NH_2$, $CH_2NHR''''$, $CH_2N(R'''')_2$, $CH_2CH_2NH_2$, $CH_2CH_2NHR$, $CH_2CH_2N(R'''')_2$, SH, $CH_2CO_2R''''$, and $CH_2CH_2CO_2R''''$, and each occurrence of R'''' is independently selected from the group consisting of maleimide, an amino acid, a small or large peptide, phosphate, sulfate, choline, and an activated ester.

9. The method of claim 8, wherein the subject is human.

10. The method of claim 8, wherein the polymer is a viscous liquid.

11. The method of claim 8, wherein the polymer is a gel.

12. The method of claim 8, wherein the step of administering comprises performing local administration of an effective amount of the polymer to a soft tissue of the subject.

13. The method of claim 12, wherein the step of administering comprises performing a single injection.

14. The method of claim 12, wherein the step of administering comprises performing at least two injections.

15. The method of claim 14, wherein the two injections are performed at least 6 months apart.

16. The method of claim 12, wherein the soft tissue is a diseased or injured synovial joint, and the polymer is used as a viscosupplement.

17. The method of claim 16, wherein the diseased or injured synovial joint is an osteoarthritic joint or a joint-induced joint.

18. The method of claim 16, wherein the diseased or injured synovial joint is a joint selected from the group consisting of knee joint, hip joint, elbow joint, ankle joint, and wrist joint.

19. The method of claim 12, wherein the soft tissue is a member of the group consisting of diseased, injured or defective vocal cord; diseased, injured or defective urinary system; diseased, injured, deformed or aging dermal tissue; and diseased, injured or defective intervertebral disc, and wherein the polymer is used as a tissue space filler.

20. The method of claim 12, wherein the subject is undergoing surgery and the soft tissue is involved in the surgery.

21. The method of claim 20, wherein the surgery is opthalmic surgery and the polymer is used as a viscoelastic agent.

22. The method of claim 20, wherein the surgery is abdominal or gynecological surgery and the polymer is used as an anti-adhesive agent.

23. The method of claim 8 further comprising a step of administering an effective amount of at least one bioactive agent to the subject.

24. The method of claim 23, wherein the bioactive agent is a member of the group consisting of a growth factor, a cytokine, a small molecule, an analgesic, an anesthetic, an antimicrobial agent, an antibacterial agent, an antiviral agent, an antifungal agent, an antibiotic, an anti-inflammatory agent, an antioxidant, an antiseptic agent, and any combination thereof.

25. The method of claim 23, wherein the bioactive agent is a member of the group consisting of collagen, fat, silicone paste, TEFLON paste, calcium hydroxyapatite, hyaluronic acid, hyaluronates, and any combination thereof.

26. The polymer of claim 1 wherein $R_2$ is COOR' and at least one occurrence of R' is $Na^+$.

27. The pharmaceutical composition of claim 4, wherein $R_2$ is COOR' and at least one occurrence of R' is $Na^+$.

28. The method of claim 8, wherein $R_2$ is COOR' and at least one occurrence of R' is $Na^+$.

29. The polymer of claim 1, wherein the polymer is:

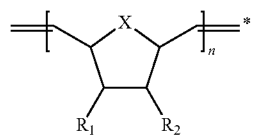

wherein:

n is an integer from 100 to 200,000; X is O; $R_1$ is H; $R_2$ is COOR'; and each occurrence of R' is independently selected from the group consisting of H and Na+.

30. The pharmaceutical composition of claim 4, wherein the polymer is:

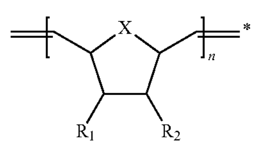

wherein:

n is an integer from 100 to 200,000; X is O; $R_1$ is H; $R_2$ is COOR'; and each occurrence of R' is independently selected from the group consisting of H and Na+.

31. The method of claim 8, wherein the polymer is:

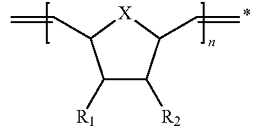

wherein:

n is an integer from 100 to 200,000; X is O; $R_1$ is H; $R_2$ is COOR'; and each occurrence of R' is independently selected from the group consisting of H and Na+.

* * * * *

UNITED STATES PATENT AND TRADEMARK OFFICE

CERTIFICATE OF CORRECTION

PATENT NO. : 8,378,064 B2
APPLICATION NO. : 12/301410
DATED : February 19, 2013
INVENTOR(S) : Grinstaff et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 608 days.

Signed and Sealed this
First Day of September, 2015

Michelle K. Lee
*Director of the United States Patent and Trademark Office*